United States Patent [19]

Fanning et al.

[11] Patent Number: 5,762,873
[45] Date of Patent: Jun. 9, 1998

[54] AUTOMATIC SAMPLE TESTING MACHINE

[75] Inventors: Mark Joseph Fanning, Florissant, Mo.; Jean-Pierre Bernard Gayral, Amberieu en Bugey, France; Clifford W. Karl, St. Louis, Mo.; Bernard Jean Marie Limon, Rignat, France; Donald Meyer, St. Peters, Mo.; Roger James Morris, St. Louis, Mo.; Ron Robinson, Bridgeton, Mo.; William Ernest Seaton, Chesterfield, Mo.; David B. Shine, University City, Mo.; Paul Springer, Florissant, Mo.; Daniel Ray Williams, Manchester, Mo.; James Clement Bishop, Columbia, Mo.; Craig Drager, Ballwin, Mo.; Thomas Burchard, Winchester, Mass.; David Chastain, Acton, Mass.; Stephen Guerrera, Milford, Mass.; Andrew Moore, Austin, Tex.; David Porat, Newton, Mass.; Arthur Rousmaniere, Andover, Mass.; Andrew Zeigler, Arlington, Mass.

[73] Assignee: bioMérieux Vitek, Inc., Hazelwood, Mo.

[21] Appl. No.: 604,672

[22] Filed: Feb. 21, 1996

[51] Int. Cl.$^6$ ........................ G01N 35/10
[52] U.S. Cl. .............. 422/65; 422/63; 422/64; 422/67; 436/43; 436/47; 436/48; 436/49; 436/179; 436/180; 436/165
[58] Field of Search ............... 422/63, 65, 64, 422/67, 68.1, 81, 100, 102, 103, 104; 436/43, 47, 48, 49, 54, 164, 165, 166, 174, 179, 180

[56] References Cited

U.S. PATENT DOCUMENTS

| | | |
|---|---|---|
| Re. 29,725 | 8/1978 | Johnson et al. ............... 422/65 |
| D. 349,861 | 8/1994 | Kanewske et al. . |
| 3,567,398 | 3/1971 | Farr . |
| 3,712,794 | 1/1973 | Farr . |
| 4,038,030 | 7/1977 | Albright et al. ............... 422/65 |

(List continued on next page.)

OTHER PUBLICATIONS bioMérieux Vitek, Inc., Brochure—Vitek® System (1995).
Manual—Vitek® Sample Testing Machine Procedures Manual, pp. 4–1 to 4–18 (1991).

*Primary Examiner*—Long V. Le
*Attorney, Agent, or Firm*—McDonnell Boehnen Hulbert & Berghoff

[57] ABSTRACT

An automatic sample testing machine for testing samples stored in test cards. The machine has a test sample positioning system for moving a tray containing a plurality of test sample cards and fluid receptacles among various stations in the machine. The machine has a diluting station for adding a predetermined quantity of diluent to the receptacles as needed. A pipetting station transfers fluid from one receptacle to another. A vacuum station is provided having a vacuum chamber moveable relative to the tray between upper and lower positions. The chamber cooperates with the tray to make a sealing engagement with the top surface of the tray when it is lowered to the lower position. A vacuum generator supplies vacuum to the chamber. When the vacuum is released from the chamber, the fluid samples are loaded into the cards from the receptacles. The test sample positioning system moves the tray to a cutting and sealing station and then to an incubation station and loads the cards one at a time into a carousel within the incubation station. A test card transport station transports the test cards from the incubation station to an optical reading station, where optical measurements (e.g., transmittance and/or fluorescence optical testing) is conducted on the wells of the card. When the card has been read, it is either moved back to the incubation station for additional incubation and reading or transferred to a card disposal system when the reading is complete.

10 Claims, 24 Drawing Sheets

U.S. PATENT DOCUMENTS

| | | |
|---|---|---|
| 4,118,280 | 10/1978 | Charles et al. . |
| 4,141,444 | 2/1979 | Kulberg et al. . |
| 4,236,825 | 12/1980 | Gilford et al. . |
| 4,265,855 | 5/1981 | Mandle et al. . |
| 4,448,534 | 5/1984 | Wertz et al. . |
| 4,626,684 | 12/1986 | Landa . |
| 4,656,007 | 4/1987 | Douchy et al. . |
| 4,673,657 | 6/1987 | Christian . |
| 4,710,352 | 12/1987 | Slater et al. . |
| 4,711,851 | 12/1987 | McNamara et al. . |
| 4,861,554 | 8/1989 | Sakuma . |
| 4,890,930 | 1/1990 | Nohso . |
| 5,008,082 | 4/1991 | Shaw . |
| 5,094,531 | 3/1992 | Garner et al. . |
| 5,192,506 | 3/1993 | Kureshy et al. . |
| 5,232,665 | 8/1993 | Burkovich et al. . |
| 5,270,006 | 12/1993 | Uchigaki et al. . |
| 5,343,909 | 9/1994 | Goodman . |
| 5,358,691 | 10/1994 | Clark et al. . |
| 5,372,782 | 12/1994 | Karkantis et al. . |
| 5,374,395 | 12/1994 | Robinson et al. . |
| 5,384,094 | 1/1995 | Schacher . |
| 5,384,095 | 1/1995 | Golz et al. . |
| 5,415,840 | 5/1995 | Sano et al. . |
| 5,417,922 | 5/1995 | Markin et al. . |

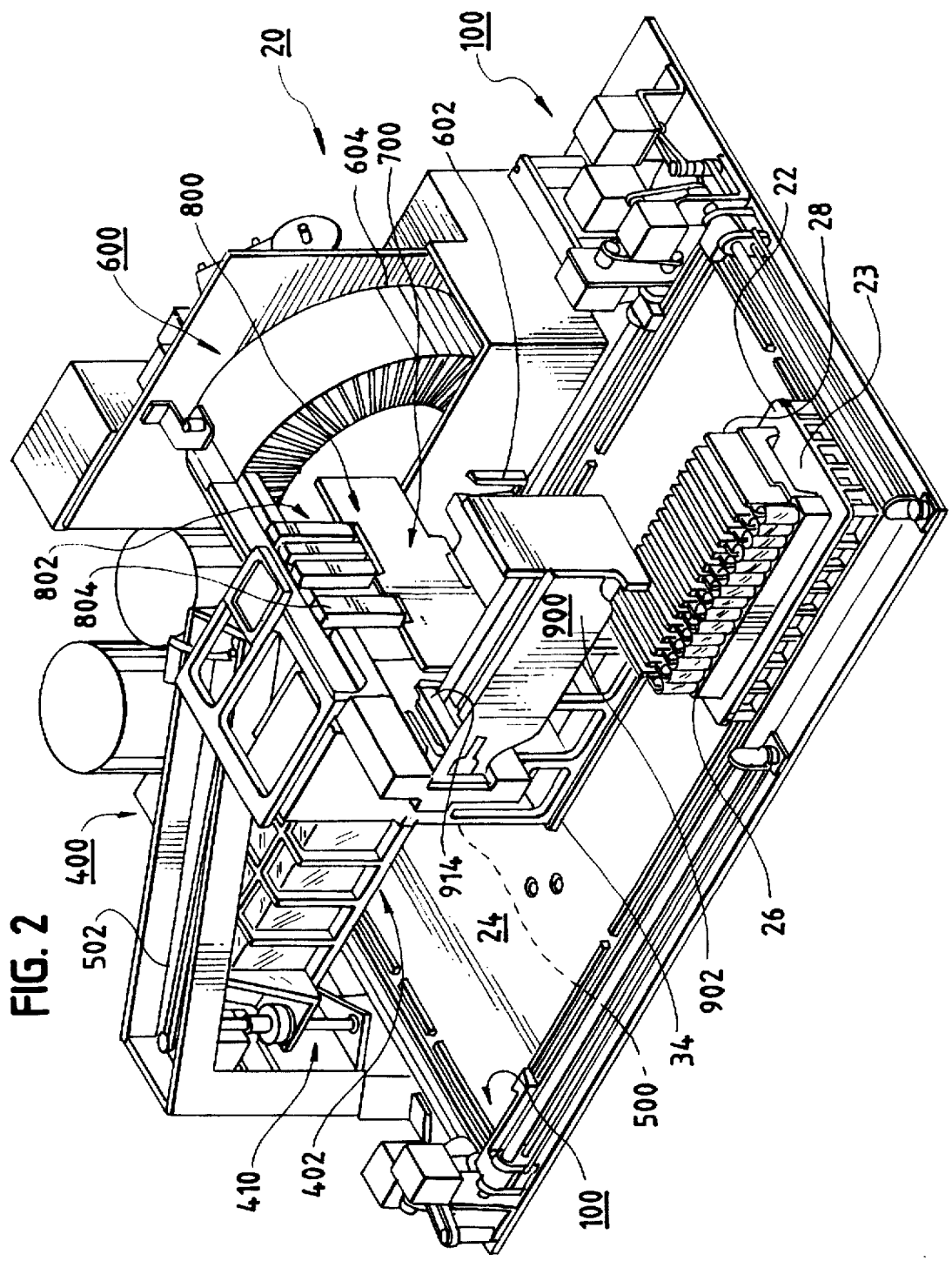

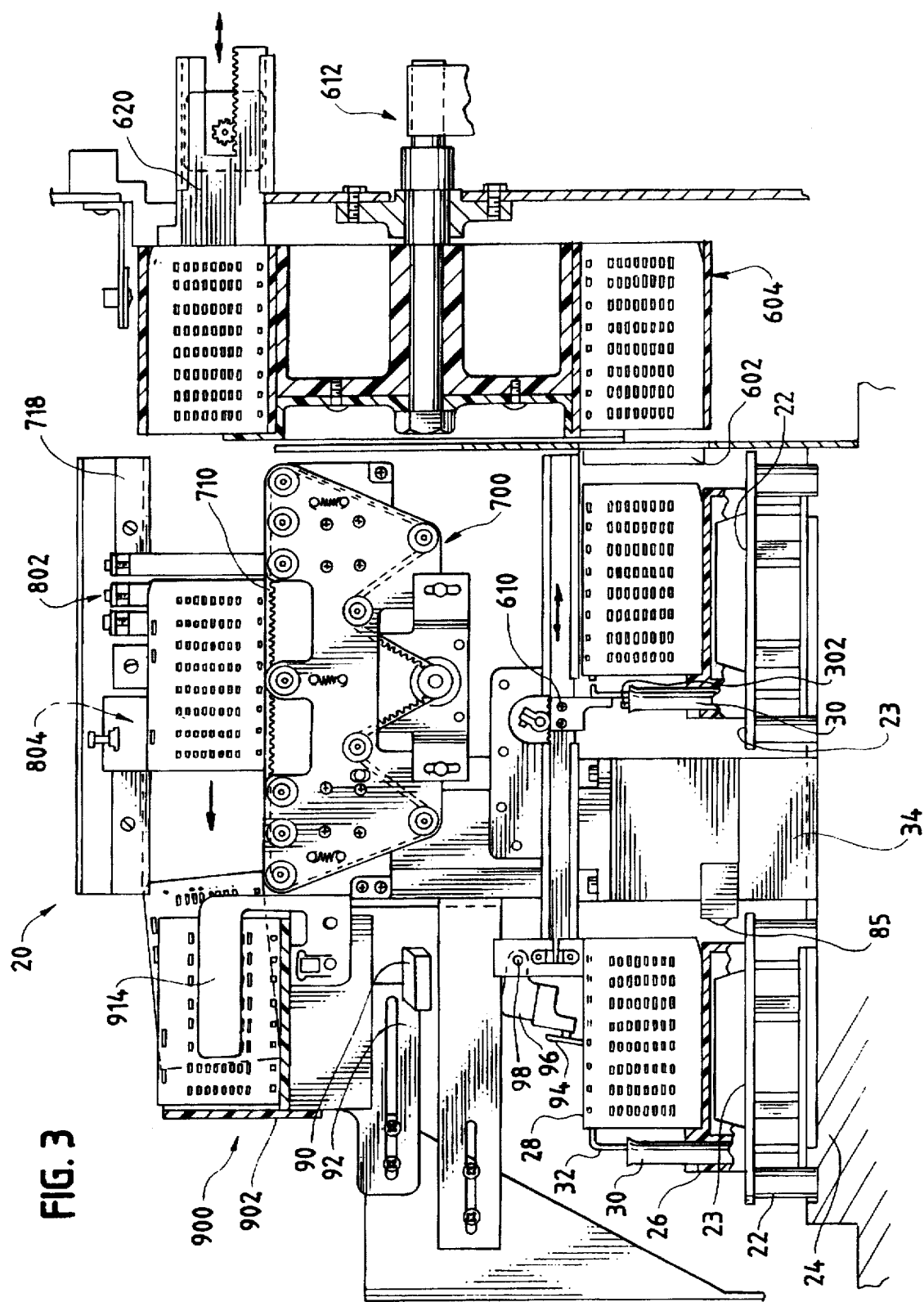

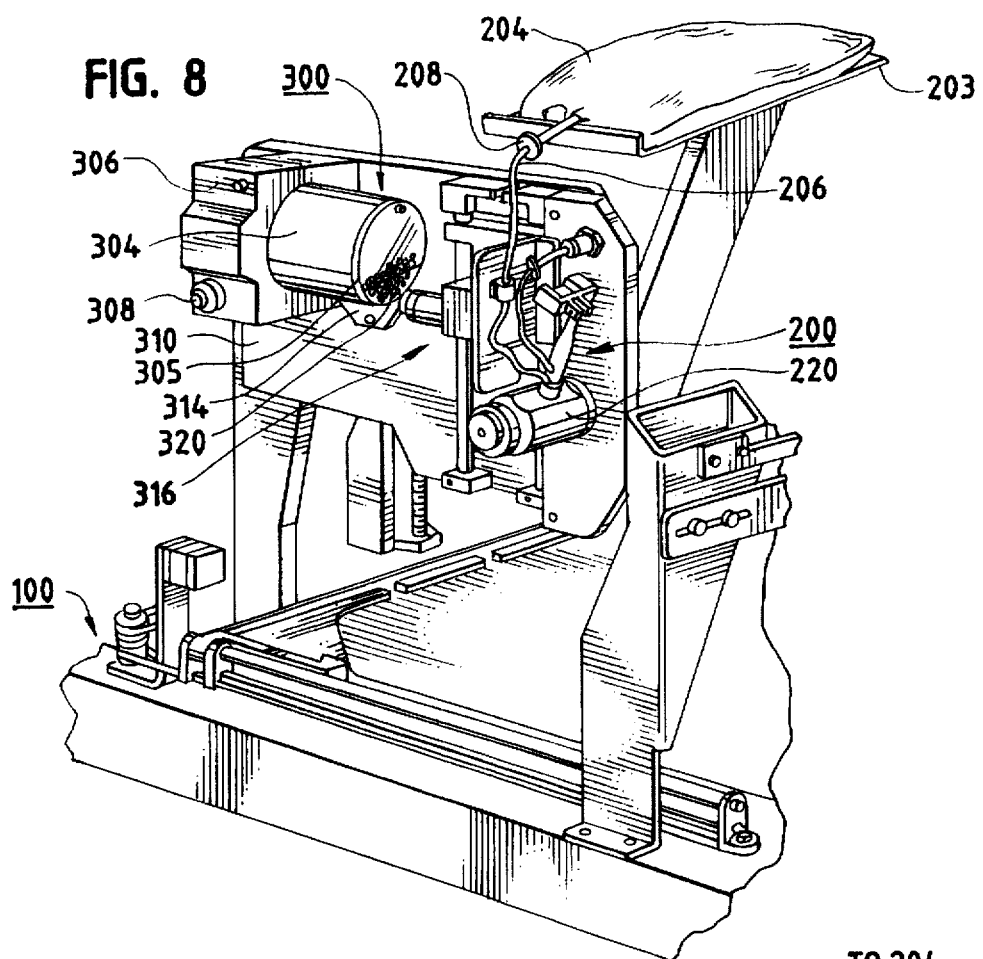
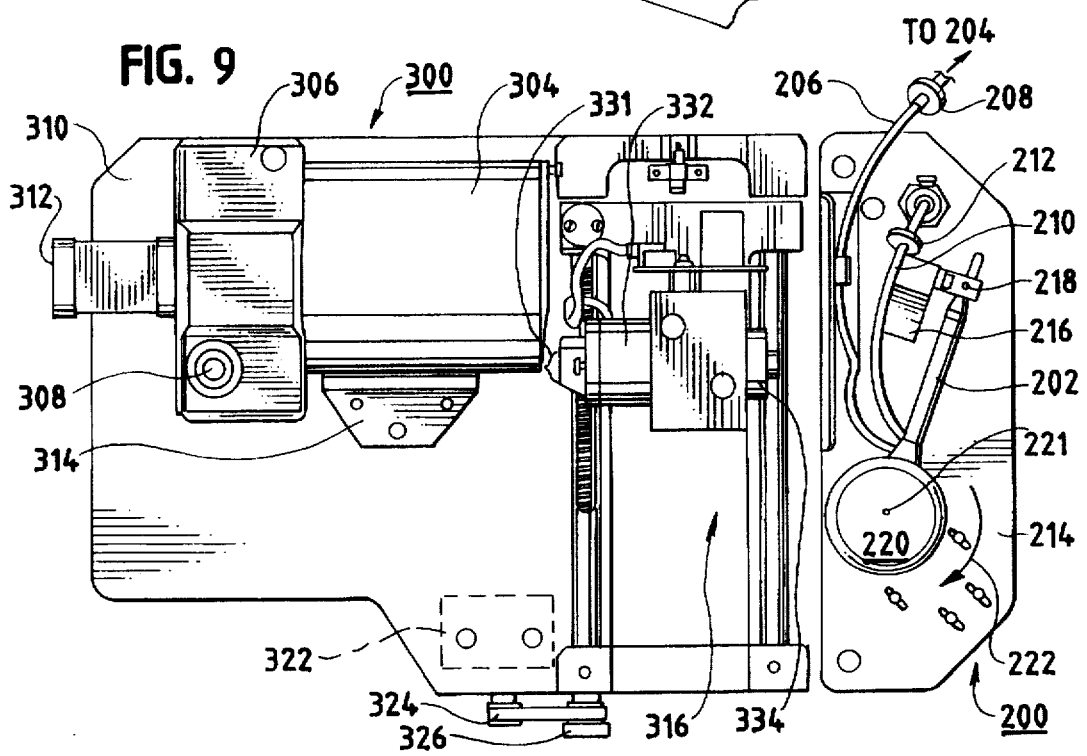

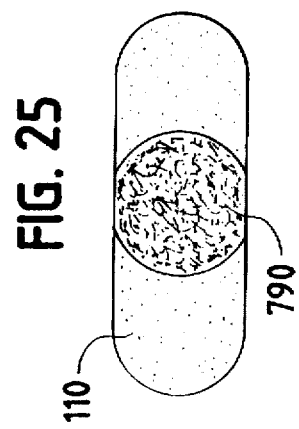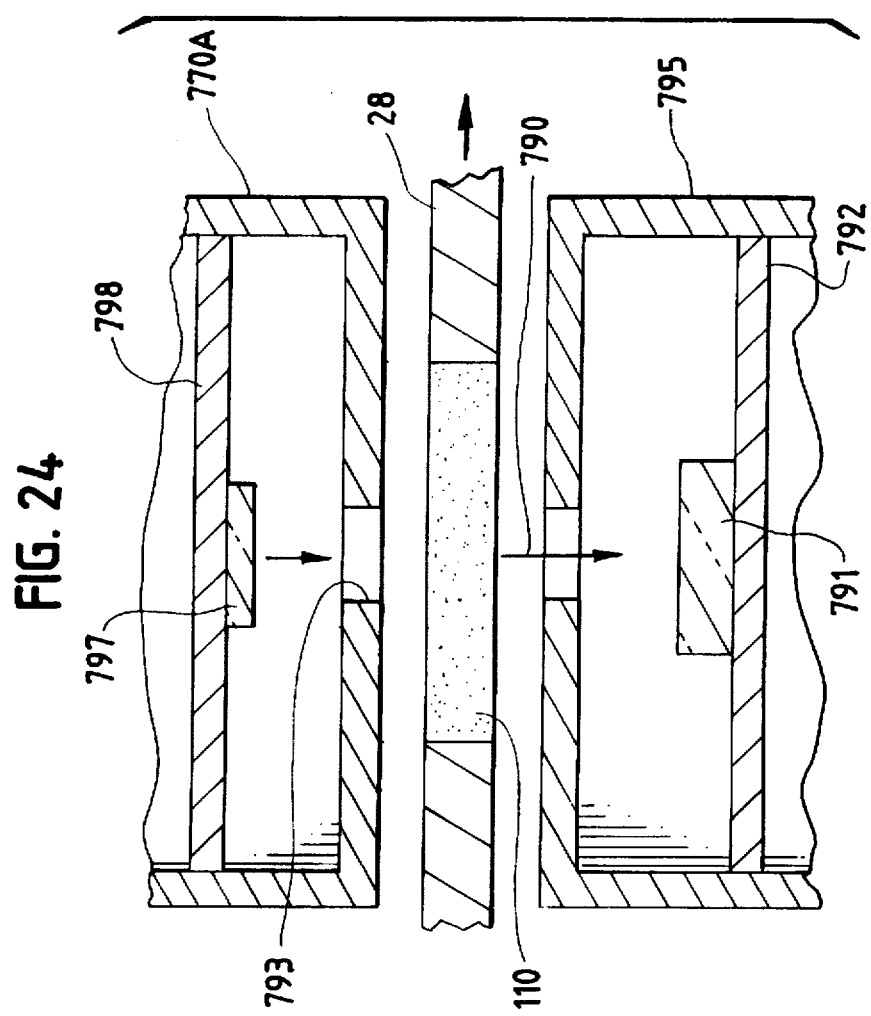

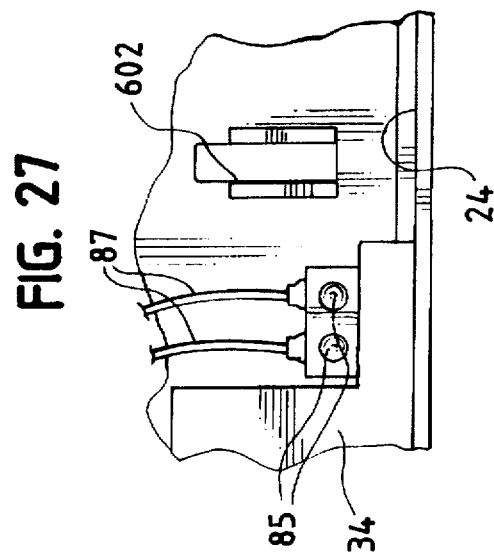
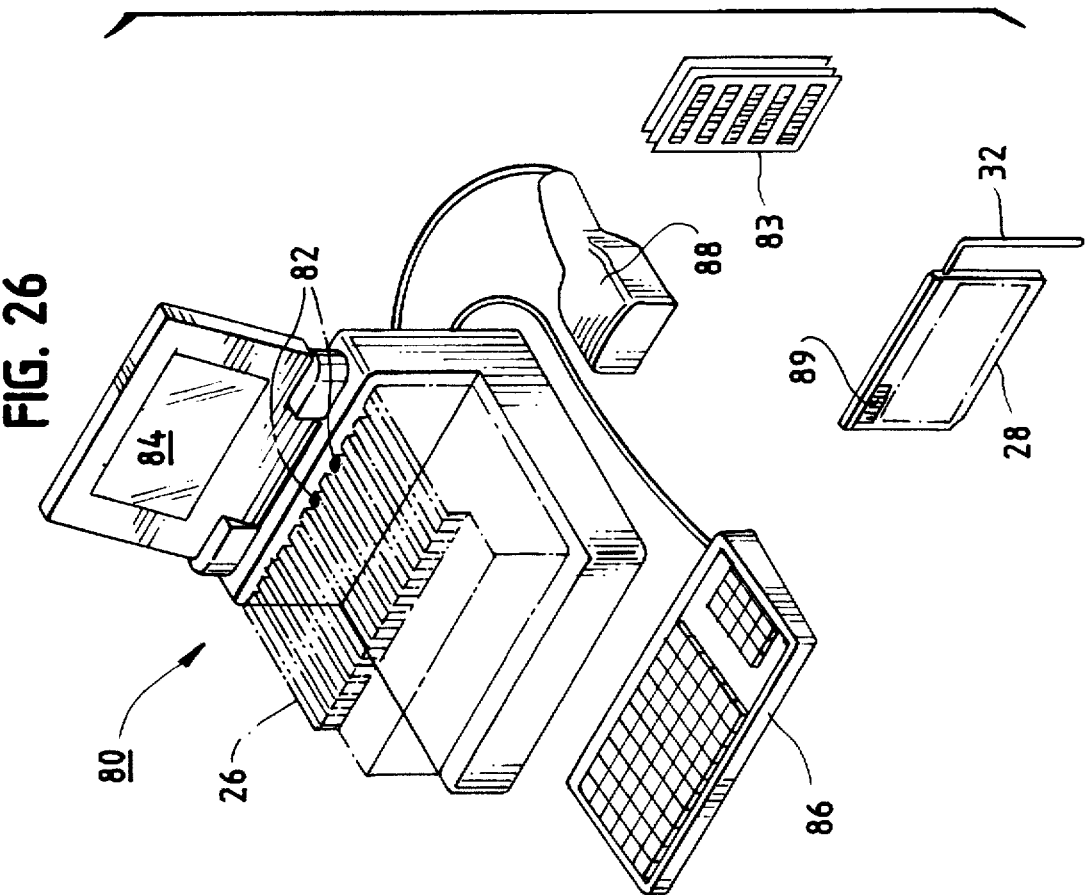

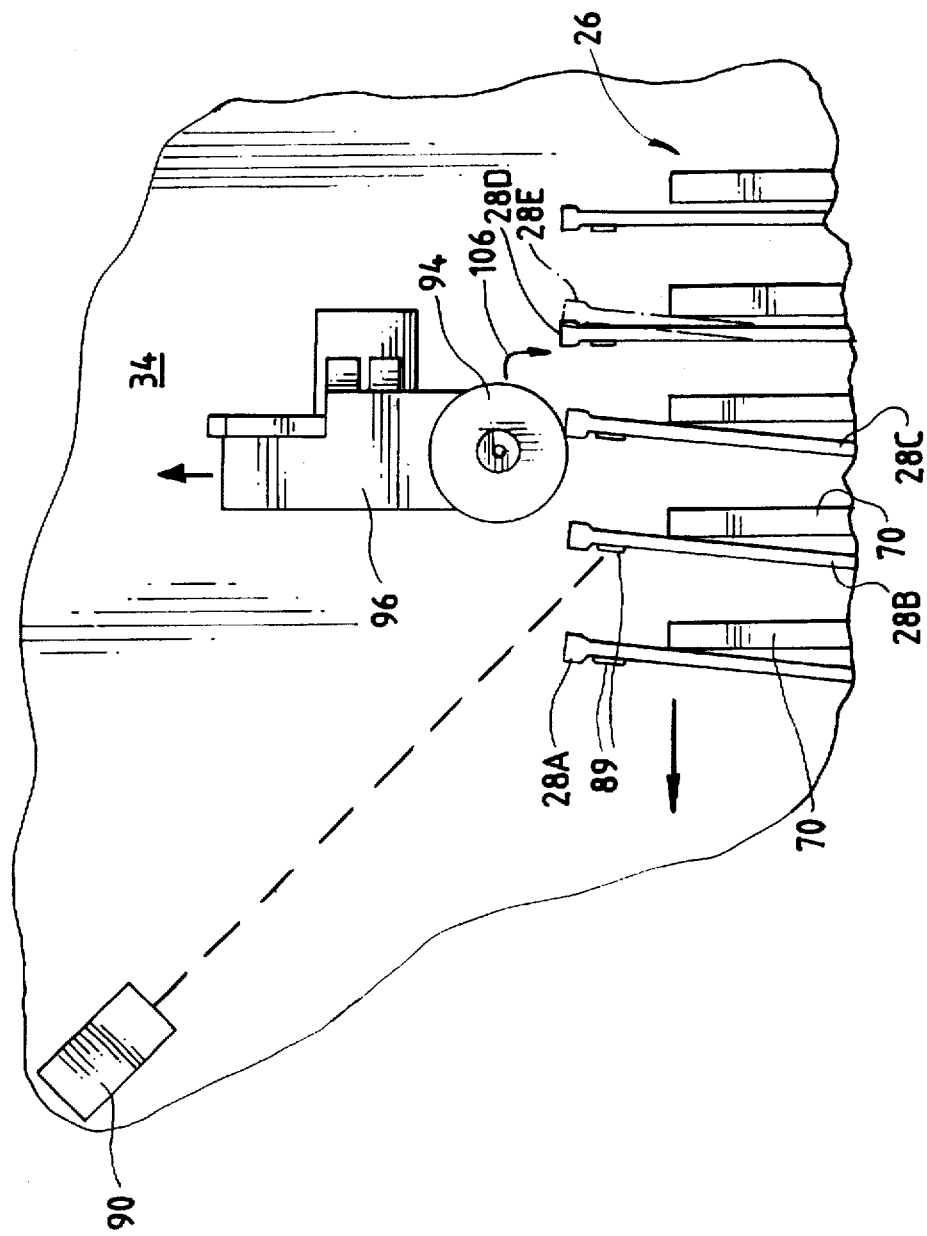

AUTOMATIC SAMPLE TESTING MACHINE

BACKGROUND OF THE INVENTION

A. Field of the Invention

This invention relates to machines and systems for automatically loading a test sample card having one or more reagent filled sample wells with fluid samples (e.g., samples containing microbiological agents), and for conducting optical analysis of the samples after reaction with the reagents. The invention is particularly suitable for use in biological, blood or chemical analysis machines, as well as immunochemistry and nucleic acid probe assay machines.

B. Description of Related Art

Biological samples can be reacted and subjected to chemical or optical analysis using various techniques, including transmittance and/or fluorescence optical analysis. The purpose of the analysis may be to identify an unknown biological agent or target in the sample, to determine the concentration of a substance in the sample, or determine whether the biological agent is susceptible to certain antibiotics, as well as the concentration of antibiotics that would be effective in treating an infection caused by the agent.

A technique has been developed for conducting optical analysis of biological samples that involves the use of a sealed test sample card containing a plurality of small sample wells. Typically, during manufacture of the cards, e.g. for microbiological analysis, the wells are filled with either various types of growth media for various biological agents, or else various concentrations of different antibiotics. The cards have an internal fluid passageway structure for allowing fluid to enter the wells of the card through a transfer tube port. An L-shaped integral transfer tube extends outwardly from the transfer tube port. The prior art method involved the manual insertion of one end of the transfer tube into the card and the other end into a test tube, and then the manual placement of the card with attached transfer tube and test tube into a vacuum filling sealing machine, such as the Vitek® Filler Sealer. The filling and sealing machine generates a vacuum, causing the fluid in the test tube to be drawn into the wells of the sample card.

After the wells of the card are loaded with the sample, the cards are manually inserted into a slot in a sealer module in the machine, where the transfer tube is cut and melted, sealing the interior of the card. The cards are then manually removed from the filler/sealer module and loaded into a reading and incubating machine, such as the VITEK® Reader. The reading and incubating machine incubates the cards at a desired temperature. An optical reader is provided for conducting transmittance testing of the wells of the card. Basically, the cards are stacked in columns in the reading machine, and an optical system moves up and down the column of cards, pulling the cards into the transmittance optics one at a time, reading the cards, and placing the cards back in the column of cards. The VITEK® reading machine is described generally in the Charles et al. patent, U.S. Pat. No. 4,188,280.

This arrangement has limitations, in that two machines, a filler/sealer and a reader, are required to process and analyze the cards. Furthermore, additional time and labor are required to conduct the complete analysis of the card.

Combining the several functions of biological sample processing and optical reading into a single automatic sample processing and reading machine poses substantial challenges. One particularly difficult challenge is to provide a way of conducting the vacuum loading of the cards, and to provide a way for moving the loaded sample card to incubation and optical reading stations. Another challenge is to design a transport system for moving the sample cards and receptacles about the machine to the various stations.

The present inventive automated sample testing machine achieves these goals by providing a machine that performs dilutions for susceptibility testing, fills the cards with the samples at a vacuum station, and seals the card by cutting the transfer tube, amd conducts incubation and optical transmittance and fluorescence analysis of the cards, all automatically. The machine is capable of conducting simultaneous susceptibility and identification testing of a sample placed in a single test tube. The machine provides for rapid, automatic identification and susceptibility testing of the sample. In a preferred form of the invention, a number of different test samples are tested simultaneously, and moved in a sample tray or "boat" around the machine among the various stations. The tray receives a cassette that contains a plurality of test tubes and associated test sample cards. The machine provides for novel pipetting and diluting stations, permitting fluids to be added to the test tubes or transferred from one test tube to another.

The machine further has a unique test sample positioning system that moves the tray (with test tubes and cards) about the machine over a base pan. The design of the positioning system is such that it permits essentially a custom configuration of stations above the base pan. Expansion of the machine to include additional carousels and reading stations, or addition types in intermediate procession stations such as dilution stations or vacuum stations, can be readily accomplished. These and still other features of the invention will be come more apparent from the following detailed description of a presently preferred embodiment of the invention.

SUMMARY OF THE INVENTION

A machine is provided for automatically testing a fluid sample delivered to reagent-filled wells of a test sample card. The machine has a loading station and a sample tray moveable within the machine from the loading station to various stations, where operations are performed on the test sample and the test sample card. The samples are placed in fluid communication with the test sample cards when the samples and cards are loaded into the tray.

The machine includes a vacuum station having a vacuum chamber moveable relative to the tray between upper and lower positions. When the vacuum chamber is lowered to its lower position, the vacuum chamber cooperates with a peripheral horizontal surface in the tray to make a sealing engagement with the tray. The vacuum station has a vacuum source for supplying vacuum to the chamber and valves for controlling the drawing of vacuum and releasing the vacuum. The fluid samples are loaded in the cards when the vacuum is released from the vacuum chamber.

In one aspect of the invention, novel vacuum loading techniques are provided for the vacuum station in order to prevent air bubbles from entering the wells of the card. These techniques include maintaining a predetermined rate of change of pressure in the vacuum pressure as vacuum in drawn, and maintaining the vacuum level at a threshold or set point for a short period of time in order to properly fill the card. After the vacuum loading process is completed, the tray is then advanced to a sealing station, where a hot cutting wire is used to cut off the transfer tube for the card and seal the interior of the card from the atmosphere.

The machine also has an incubation station for incubating the card. A test sample positioning system is provided for moving the tray from the loading station to the vacuum station and from the vacuum station to the incubation station. An optical reading station is provided for reading the cards during incubation of the cards in the incubation station. A test sample card transport station is provided for transporting the test sample card from the incubation station to the optical reading station where the optical reading station conducts optical analysis of the sample loaded into the test sample card.

In a preferred form of the invention, a diluting station is provided for selectively adding diluent to the receptacles or test tubes in the tray. A pipetting station is also provided for transferring fluid samples from one receptacle to another. The diluting and pipetting stations are preferably placed close to each other, so as to permit simultaneous pipetting and diluting operations to be performed on the receptacles in the tray.

In another aspect of the invention, the sample cards and receptacles are loaded onto a cassette, and the cassette placed in the tray in the machine. A stand-alone information system is provided for associating fluid or test sample and test card information with the cassette. A machine-readable memory storage device is applied to the cassette. A machine-readable indicator is applied to the sample cards and is identified with each of said test sample cards. An information loading station reads the machine-readable indicators for a plurality of the sample cards when they are loaded in the cassette, and stores information regarding said test sample cards onto the machine-readable memory storage device. As the cassette is moved within the automated sample testing machine, it passes by an information retrieving station which retrieves information stored in said machine-readable memory storage device.

In a preferred embodiment, the information loading station has a memory, a human interface for transferring testing information input from a user of the system into the memory, a reader for the machine readable indicator, and a software program responsive to the human interface for associating in the memory testing information from the user with the machine-readable indicator applied to the test sample card.

BRIEF DESCRIPTION OF THE DRAWINGS

Presently preferred embodiments of the invention are depicted in the drawings, wherein like reference numerals refer to like elements in the various views, and wherein:

FIG. 2 is a perspective view of the machine of FIG. 1, with the diluting and pipetting stations removed to better illustrate the vacuum station of the machine, and with the stacking disposal station added.

FIG. 3 is an end view of the machine, partially in section, as seen from the right-hand side of the machine looking toward the center mount.

FIG. 8 is a more detailed perspective view of the diluting and pipetting stations of FIG. 1.

FIG. 9 is an elevational view of the diluting and pipetting stations of FIG. 8.

FIG. 24 is a sectional view of one of the transmittance sources of FIG. 22, showing the relationship between the LED transmittance light source, sample well, and photodiode detector.

FIG. 25 is an elevational view of the sample well and LED output for the transmittance substation of FIG. 22.

FIG. 26 is a perspective view of a stand-alone data input station that loads information from bar codes placed across the top of the cards 28 onto a pair of touch memory buttons.

FIG. 27 is a illustration of a portion of the center mount and base pan of FIG. 1, showing the placement of a touch memory button reading station along the side of the center mount. The two contacts of the reading station touching the two touch memory buttons on the side of the cassette as the boat and cassette are moved past the station.

FIG. 28 is a side view of a portion of the cards and cassette as it passes by the bar code reading station;

DETAILED DESCRIPTION OF THE PREFERRED EMBODIMENT

Overview of Preferred Automatic Sample Testing Machine

Figure 1:
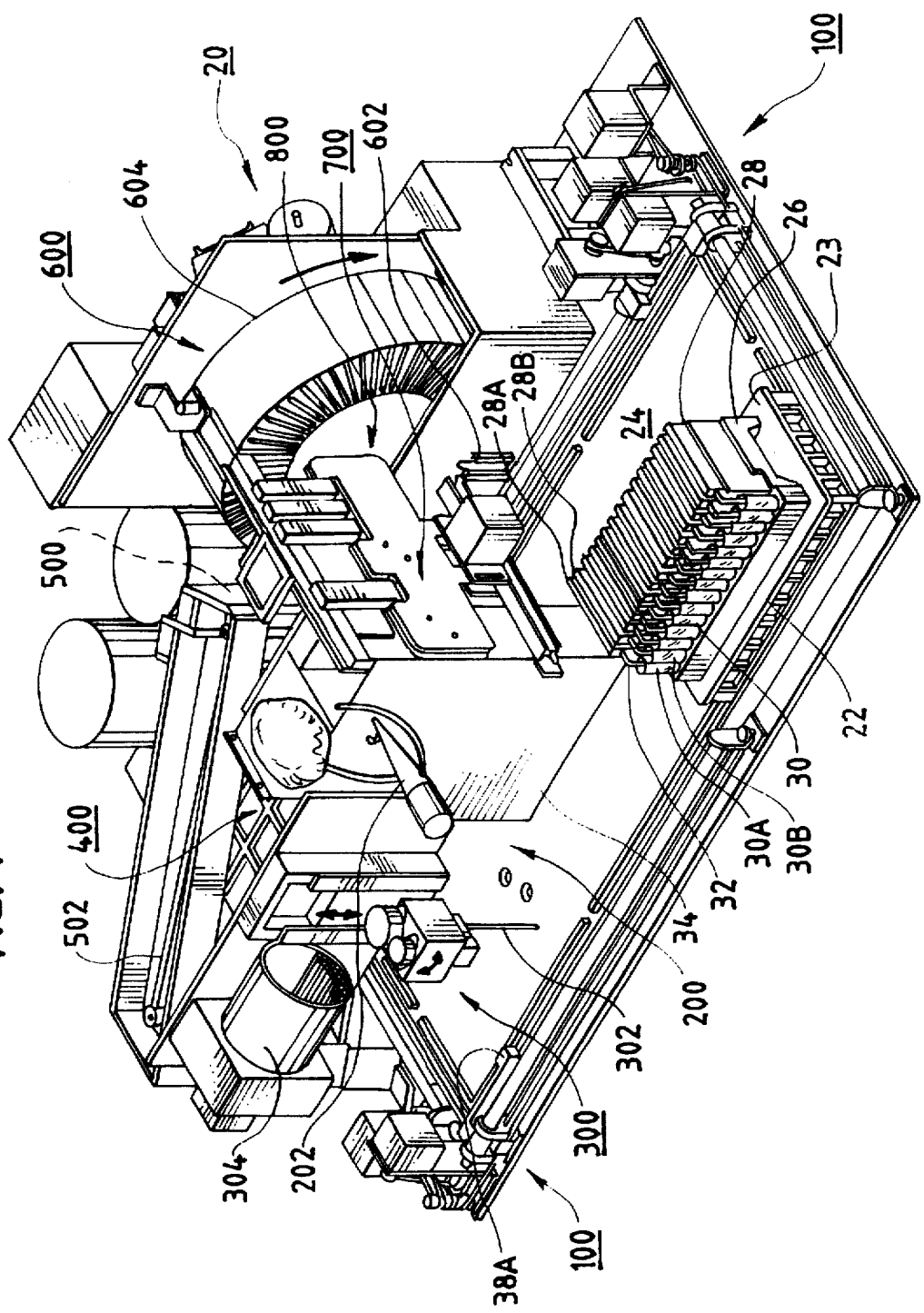
FIG. 1 is a perspective view of a preferred automatic biological sample testing machine in accordance with the invention. The card disposal station is removed in order to more clearly show the other features of the machine.
Figure 1A:
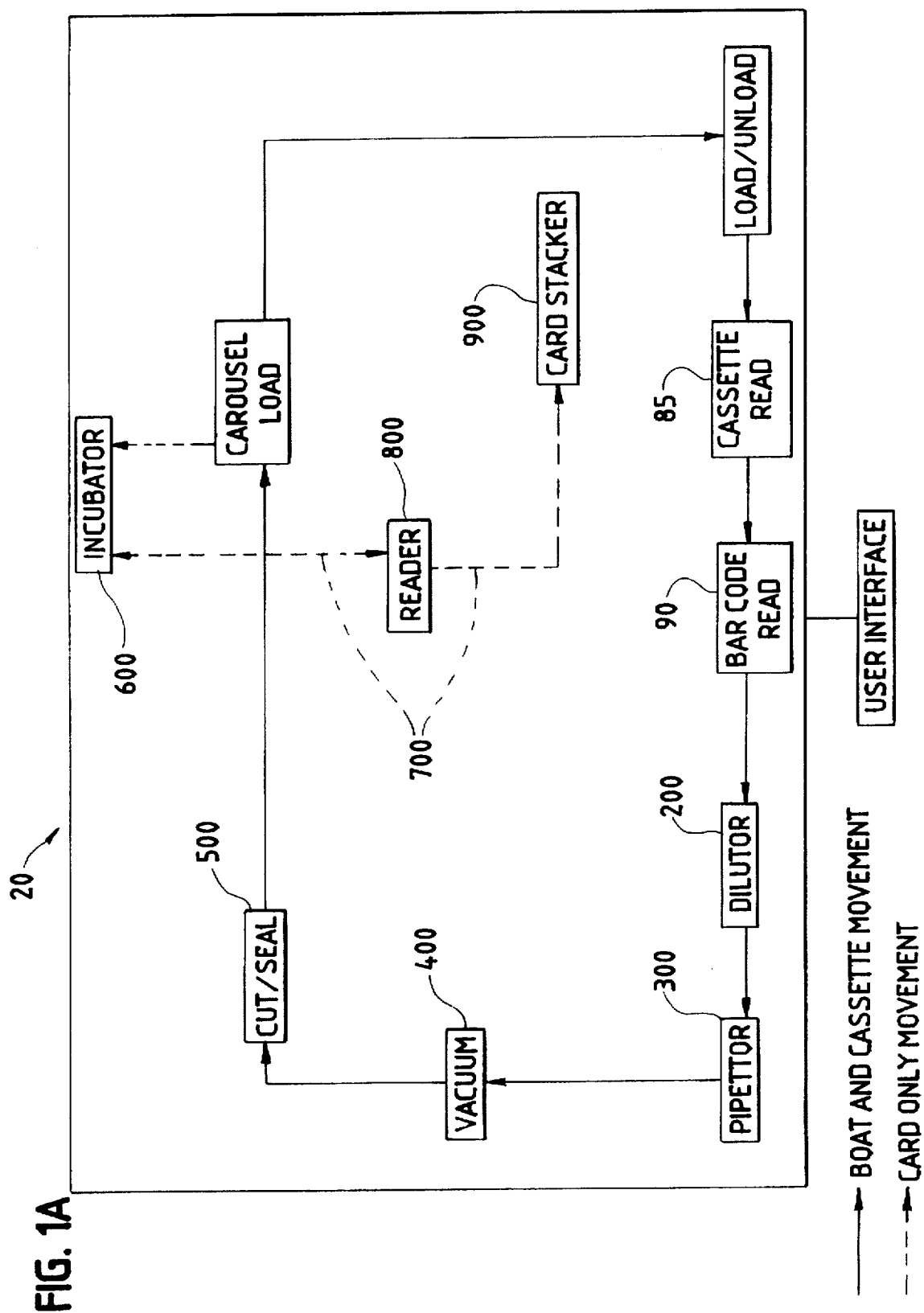
FIG. 1A is a block diagram of the all of the principal stations in the machine of FIG. 1.

FIG. 1 is a perspective view of a biological sample testing machine 20 that conducts analysis of test sample filled cards 28 according to a preferred embodiment of the invention. In FIG. 1, a stacking card disposal station for the cards 28 has been removed in order to illustrate the other components of the machine. The card disposal station 900 is shown in FIG. 2. FIG. 3 is an end view of the machine, partially in section, showing the position of the test sample cards 28 as they are processed in several of the stations in the machine 20. FIG. 1A is a block diagram of the machine 20 as whole, showing the layout of the stations and the path of the boat and cassette and test sample cards through the machine in a preferred embodiment of the invention.

Referring now primarily to FIGS. 1, 1A and 3, the biological sample testing machine 20 includes a biological test sample positioning system 100, consisting of four independent motor-driven paddles, which is designed to pull a sample tray 22 (referred to herein as a "boat") incorporating a cassette 26 across a base pan 24 around the machine 20 to several discrete stations, where various operations are performed on the cards and receptacles in the cassette 26. Prior to the start of the procedure, a technician loads a cassette 26 with a plurality of test cards 28 and receptacles such as test tubes 30 containing biological or control samples to be tested. Each test card 28 has an L-shaped transfer tube 32 protruding therefrom for permitting the fluids containing biological samples to be drawn from the test tubes 30 into the reagent-filled wells of the test cards 28. The technician places the loaded cassette 26 into the boat 22 at a loading station for the machine, such as the front, right hand corner of the base pan 24 shown in FIG. 1. The combined boat 22 and loaded cassette 26 are then moved as a unit over the surface of the base pan 24 about the machine 20 by the test sample positioning system 100.

In a typical microbiological testing scenario, described below for purposes of illustration but not limitation, the test cards 28 come in two varieties: (1) identification cards, in which particular different growth media are placed in each of the wells of the card 28 when the cards are manufactured, and (2) susceptibility cards, in which different concentrations of different antibiotics are placed in each of the wells of the card 28. The identification cards are used to identify the particular unknown biological agent, i.e., microorganism, present in the sample. The susceptibility cards are used to determine the susceptibility of the biological agent to various concentrations of antibiotics or other drugs. In the test procedure described below, identification and susceptibility tests can be performed on a single sample in one cycle of operation of the machine 20. To accomplish this, the cassette 26 is loaded such that a test tube 30A containing a biological sample, connected via a transfer tube 32 to an identification card 28A, is placed adjacent to a test tube 30B connected via a transfer tube 32 to a susceptibility card 28B.

The cards 28 preferably contain bar codes as well as other identifying indicia on the card for reading by a bar code reader built into the machine 20. The bar codes are unique to each card, and identify card information such as card type, expiration date, and serial number, and are used to correlate test data and/or results from the cards with the patient and the biological sample. In addition, the entire boat or cassette may have sample information for all of the cards loaded in the cassette stored on one or more memory devices affixed to the cassette 26, such as a memory button or "touch button" available from Dallas Semiconductor Corp., 4401 S. Beltwood Parkway, Dallas Tex.

In the representative example shown in FIG. 1, seven or eight of the test tubes 30 in the boat 22 contain biological samples, and are in fluid communication with identification cards 28A by the straw-like transfer tube 32. The biological sample test tube 30A and its associated identification card 28A can be thought of as a set. The biological sample test tubes and identification cards are typically arranged in an alternating pattern in the cassette 26. Each biological sample test tube 30A and identification card 28A set is adjacent to an empty test tube 30B placed in communication with a susceptibility card 28B via a transfer tube 32. It will be appreciated that the cards and associated test tubes could be ordered in any order in the cassette 26 depending on the particular testing requirements for the samples. For example, the cards could be arranged as follows: identification (ID), susceptibility (SU), ID, ID, ID, SU, SU, ID, SU .... Further examples would be all identification cards and all susceptibility cards.

The test sample positioning system 100 operates to move the boat 22 and cassette 26 over the base pan 24 first to a diluting station 200. The diluting station contains a rotating shot tube 202, by which a predetermined volume of diluent (such as saline solution) is added to the empty susceptibility test tubes in the cassette 26, e.g. test tube 30B. As the leading edge of the boat 22 is moved to the left during this process, it passes under a pipetting station 300. The pipetting station 300 includes a mechanism that automatically removes a pipette 302 from a source of pipettes 304, lowers the pipette 302 into the biological sample test tube 30A, and removes with vacuum a predetermined volume of biological fluid from the biological sample test tube 30A using the pipette 302.

The test sample positioning system 100 then moves the boat 22 to the left by an amount equal to the separation distance between adjacent test tubes 30A and 30B, e.g. 15 mm. The pipetting station 300 then lowers the pipette 302 containing the biological fluid from the biological sample test tube 30A into the adjacent susceptibility test tube 30B (having already received a quantity of diluent from the diluting station 200), expels the fluid into the test tube 30B, and drops the pipette 302 into the susceptibility test tube 30B. The process of movement of the boat 22 by the test sample positioning system 100, adding diluent to the susceptibility test tubes 30B at the diluting station 200, and transferring of biological samples from the biological sample test tubes 30A to the adjacent susceptibility test tubes 30B at the pipetting station 300, continues until all of the identification and/or susceptibility test tubes sets (if any) in the boat 22 have been so processed. By virtue of the close spacing of the pipetting station 300 and the diluting station 200, simultaneous diluting and pipetting operations can be performed on multiple test tubes in a single boat 22. After the last pipetting operation has been performed, the test sample positioning system 100 then moves the boat 22 all the way to the left-hand edge of the base pan 24.

It will be understood by persons skilled in the art that the cassette 26 may be loaded entirely with biological samples in the test tubes 30 and identification cards 28, such as the case where a batch of biological samples are to be tested to identify the contents of the samples. In this example, the diluting and pipetting operations are not necessary. However, in other types of sample testing, other diluents or fluids may be added to or withdrawn from the test tubes. In the example of where no diluting or pipetting operations are performed (e.g., where the pipetting and diluting operations were performed off-line), the cassette 26 is loaded with test tubes and cards, and the positioning system 100 would simply move the boat 22 and loaded cassette 26 directly past the diluting station 200 and the pipetting station 300 without stopping, all the way to the left hand edge of the base pan 24.

Once at the left hand edge of the base pan 24, the test sample positioning system 100 operates to move the boat 22 along the left hand edge to a vacuum station 400. The vacuum station 400 is seen better in FIG. 2, which is a perspective view of the machine 20 with the diluting station 200 and the pipetting station 300 removed, and in FIGS. 4 and 5. At the vacuum station 400, a vacuum chamber 402 is lowered onto the boat 22 such that the bottom surface of the vacuum chamber 402 sealingly engages the top peripheral surface 23 of the boat 22. The vacuum chamber has hoses 406, 408 (FIG. 4) that are in communication with a conventional vacuum source for the machine (not shown). Vacuum is applied to the chamber 402 under microprocessor control, causing air in the interior of the test sample cards 28 to evacuate out of their associated test tubes and to be withdrawn from the chamber 402. The vacuum cycle is precisely managed to optimize filling using a closed loop servo system to regulate the rate of change of vacuum and the timing of the complete vacuum cycle. After a predetermined period, the chamber 402 is vented to atmosphere under microprocessor control. The venting of the cards causes the fluid in the test tubes 30 to be drawn into the cards 28, filling the wells in the cards 28. After the chamber 402 is vented, the chamber is raised up by a vacuum chamber drive mechanism 410 so as to permit the boat to be moved to the other stations of the machine 20.

Figure 4:
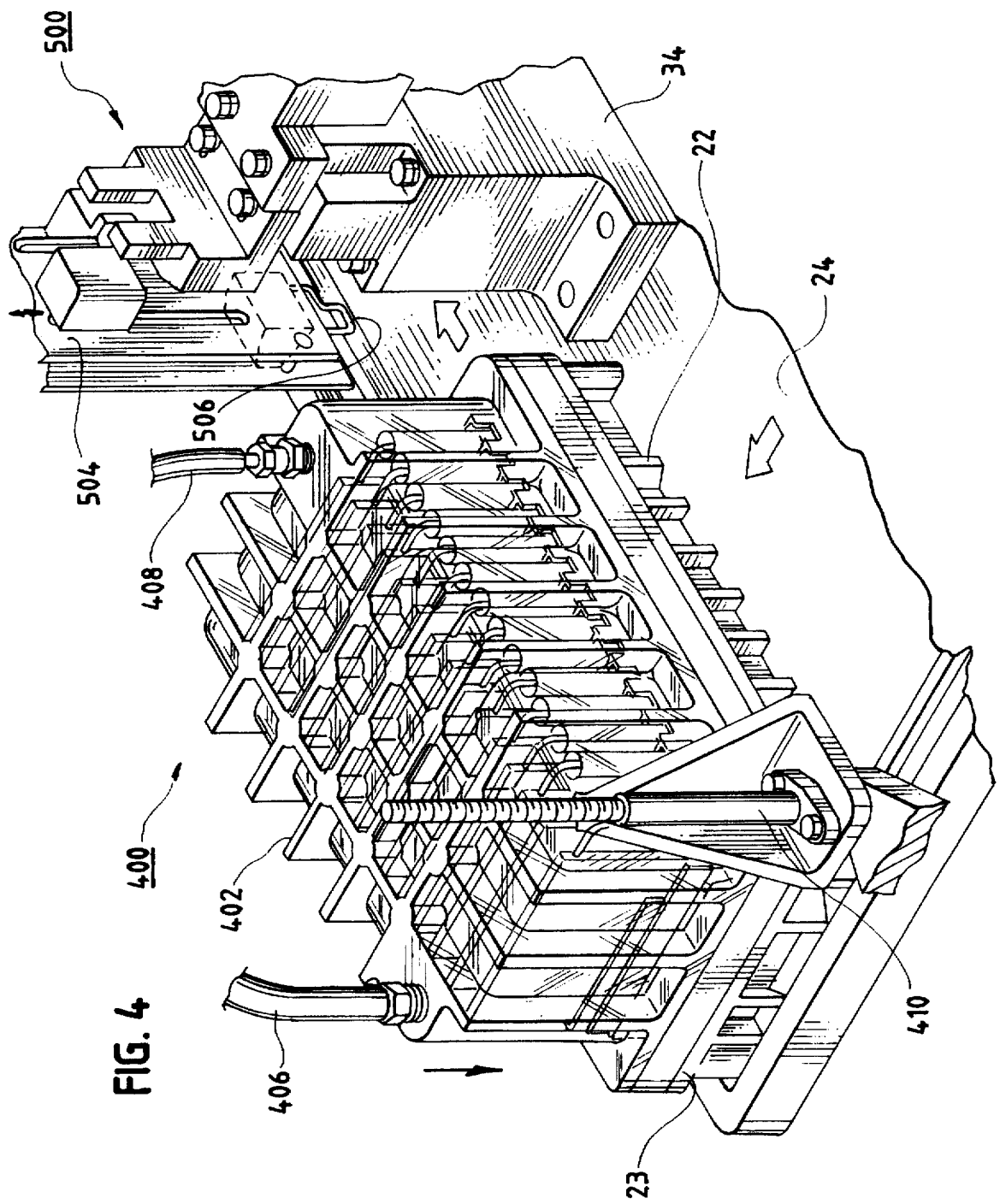
FIG. 4 is a detailed view of the vacuum chamber of the vacuum station of FIG. 2 engaging the top surface of the boat, as it would be when the fluid samples are loaded into the cards.
Figure 5:
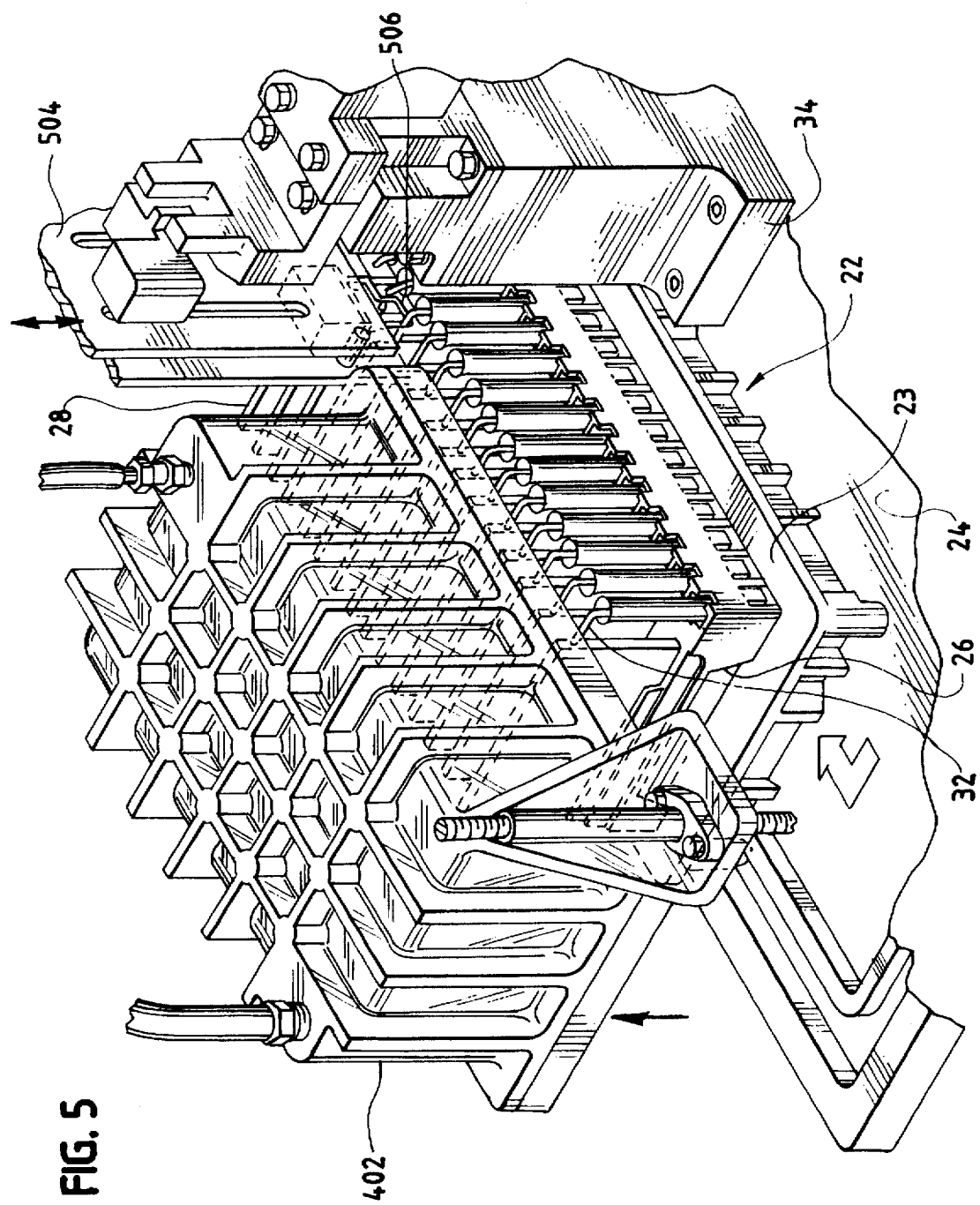
FIG. 5 is a detailed view of the cut and seal station, showing the hot cutting wire cutting through the transfer tubes for the cards when the boat is advanced past the hot cutting wire, thereby sealing the interior of the cards.

The test sample positioning system 100 then operates to advance the boat 22 to the right across the rear of the base pan 24 to a cut and seal station 500, located behind the center mount 34 in FIGS. 1 and 2. Referring to FIGS. 4 and 5, the cut and seal station 500 consists of a hot cutting wire 506 and attached support plate 504, and a drive mechanism 502 (e.g., stepper motor, drive belt and lead screw) that lowers the cutting wire and support plate 504 to the same elevation as the top portion of the transfer tubes 32 adjacent to where the transfer tubes 32 enter the test cards 28. As the boat 22 is advanced past the cut and seal station 500, the transfer tubes 32 are forced past the hot cutting wire 506. With the assistance of fore and aft constraints placed on the movement of the cards 28 by the walls of the cassette 26, and the lateral constraints on the movement of the card 28 by the cassette and wall structures of the machine 20, the hot cutting wire cuts the transfer tubes 32 by melting of the transfer tube material as the boat 22 is slowly advanced past the hot cutting wire 506. A small stub of transfer tube material is left on the exterior of the card 28. The stub seals the interior of the card 28 from the atmosphere (except for possible diffusion of gasses such as oxygen through the tape covering the sample wells). When the boat is advanced past the station 500, the wire 506 is raised up to its upper position.

Referring to FIGS. 1 and 3, the test sample positioning system 100 then advances the boat 22 across the rear of the base pan 24 behind the center mount 34 to a carousel incubation station 600. A reciprocating rack and pinion driver 610 is mounted to the center mount 34 opposite a slot 602 in the machine that pushes the cards off the cassette 26 one at a time through the slot 602 into a carousel 604. The carousel 604 is housed in an enclosure that is maintained at an appropriate incubation temperature for the particular assay, for example, 35 degrees C. The enclosure is partially broken away in FIGS. 1 and 2 in order to show the carousel 604. The carousel 604 is rotated by a drive system 612 in synchronism with the movement of the boat 22 over the rear of the base pan 26 by the test sample positioning system 100, so as to place the next slot in the carousel 604 in line with the slot 602 opposite the next card in the cassette 26. If the carousel is only going to be partially loaded with cards, the operating system of the machine may control the carousel 604 rotation to load the cards into non-adjacent slots to equally distribute the cards in the carousel in order to balance out the weight distribution in the carousel 604. For example, where the carousel has 60 slots and only 30 cards are to be processed, the cards could be loaded into every other slot.

Additional incubation capacity required for processing a larger number of cards at one time can be provided by adding an additional incubation station(s) to the rear of the basepan, and adjusting the dimension of the base pan and drive system components as necessary. Additional optics stations may be provided for additional carousels. For example, if the carousel 604 has sixty slots and each cassette holds 15 cards, four boats can be processed at once. If a second carousel is added, up to 120 cards could be processed at once. Of course, different capacities could be provided for the cassette 26 and the carousel 604. Additional pipetting and diluting capacity and vacuum chambers or other functions could be provided as well.

After all of the cards 28 have been loaded into the slots of the carousel 604, the boat 22 is advanced along the right hand edge of the base pan 24 back to its starting position (shown in FIGS. 1 and 2) or to an exit position for removal of the cassette 26 (containing the test tubes, pipettes 302, if any, and transfer tubes remnants) and receipt of a new cassette. Alternatively, the boat 22 could be moved to an exit station located, for example, in the rear or right hand side of the base pan 24.

As the cards 28 are being incubated in the incubation station 600, the cards are periodically, sequentially pushed out of the slots of the carousel 604 at the top of the carousel 604, one at a time, by a reciprocating rack and pinion driver 620 and an associated stepper motor. The cards 28 are moved by an optical scanner card transport station 700 past a fluorescence and transmittance optics station 800 having a transmittance substation 802 and a fluorescence substation 804. The wells of the card 28 are selectively subject to sets of transmittance and/or fluorescence optical testing according to the analysis needed to be performed by the transmittance and fluorescence optics station 800. The transmittance and fluorescence optics station 800 includes detectors and processing circuitry to generate transmittance and fluorescence data for the wells in the cards 28, and to report the data to a central processing unit for the machine 22. If the test is not complete, the transport station 700 moves the card 28 back into its slot in the carousel 604 for more incubation and additional reading.

Typically, each card will be read every 15 minutes as the carousel makes one revolution. Typical incubation times for the cards 28 are on the order of two to eighteen hours, consisting of roughly four transmittance and/or fluorescence data sets per hour for each of the wells in the card 28 subject to the optical analysis requirements.

After the testing is complete, the cards are moved by the optical scanner transport system 700 into a card output station 900 shown in FIG. 2 and FIG. 3. The card output station 900 consists of a detachable tray or magazine 902 and associated support structure that is positioned to the side of the optical station 800 at approximately the same elevation as the optical station 800. The station 900 has a pressure slide that 914 that is moveable within the magazine 902 and a constant force spring biasing the pressure slide towards the front of the magazine. The cards are stacked in the magazine between the pressure slide 914 and oppositely opposed resilient snap elements integrally formed in the sides of the magazine 902. The technician removes the magazine 902 from the machine 20 as needed or when the magazine is full of cards, empties the cards into a suitable biohazard disposal unit, and replaces the magazine 902 back into the machine 20.

Test sample positioning system 100

Figure 6:
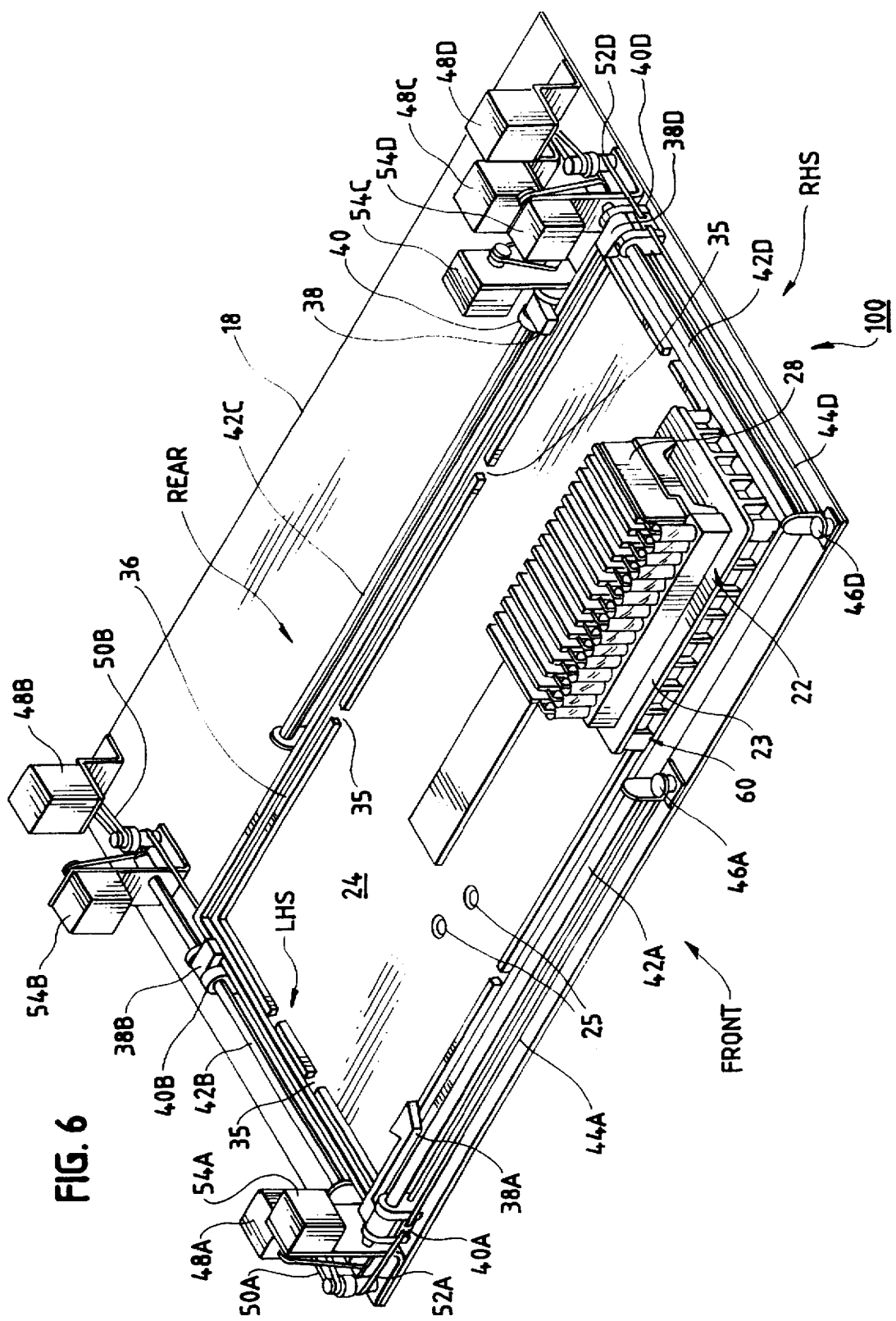
FIG. 6 is a detailed perspective view of the test sample positioning system of FIGS. 1 and 2.

Referring now in particular to FIG. 6, the test sample positioning system 100 will be described in detail. The system 100 is shown in a perspective view in FIG. 6 with all of the stations mounted to the center mount 34 and the incubation station 600 removed in order to more clearly illustrate the components of the positioning system 100.

The system 100 has a base pan 24 mounted to a table support structure 18, across which the boat 22 is pulled from station to station in the machine 22. The base pan 24 in the preferred embodiment is of rectangular shape having four sides at right angles to each other: a front side, a left hand side (LHS), a rear side, and a right hand side (RHS). The four sides allow the boat 22 to be moved clockwise in a loop about the machine back to its starting position at a loading station (shown in FIGS. 1–2) after all of the operations on the sample card 28 have been completed. However, the inventive principles of the test sample positioning system are applicable to other geometries for a base pan 24. Additionally, the paddles and motors are capable of moving the boat 22 in a counter-clockwise direction.

The boat 22 has four downwardly depending feet 72 at its four corners which fit in a pattern of track sections comprising grooves 36 formed between a set of raised ridges 37 and a raised rim 39 extending around the perimeter of the base pan 24. The grooves 36 help prevent any rotation of the boat 22 as the boat 22 is pulled over the base pan 24.

Figure 7:
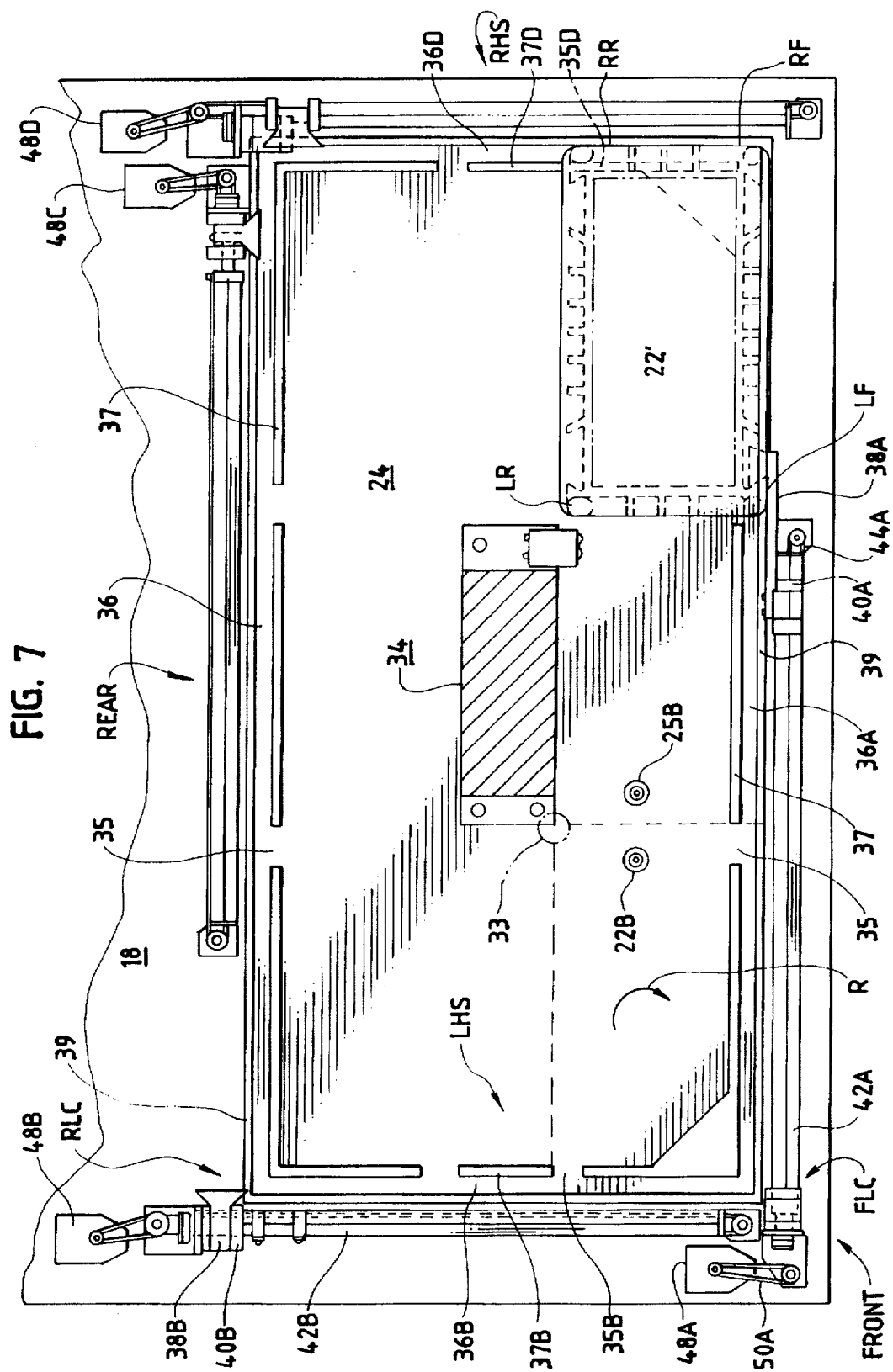
FIG. 7 is a plan view of the base pan of FIG. 6.

When the boat 22 is initially located at the loading station, as shown in FIG. 7, the left front LF and right front RF feet of the boat 22 are positioned in groove 36A, the right rear (RR) foot 72 is in groove 36D, with the RF foot at the intersection of grooves 36A and 36D. A plurality of slots 35 are provided in the raised ridges 37 so as to permit the feet of the boat 22 to move through the ridges 36 as the boat 22 is moved about the base pan 24. For example, slot 35D permits the right rear RR foot to move past raised ridge 37D, and slot 35B permits the left rear LR foot to move past the ridge 37B into the groove 36B. The center mount has a corner 33 that is preferably given a sharp contour, as shown, so as to prevent the boat from undergoing rotation as it is slid along the left hand side of the base pan.

In order to move the boat 22 clockwise about the base pan, four independent drive systems are provided for moving the boat 22. Each drive system moves the boat 22 in one direction along one of the four sides of the base pan 24. Referring now in particular to FIG. 6, a first drive system is provided for moving the boat 22 along the front edge of the base pan 24, and consists of a rotatable shaft 42A having a square cross section, a collar 40A slideably mounted the shaft 42A, a drive belt 44A mounted to the collar for sliding the collar 40A along the shaft 42A, a stepper drive motor 48A driving a belt 50A, a pulley 52A for moving the drive belt 44A back and forth along the front edge of the base pan, and a second pulley 46A for the drive belt 44A. A paddle 38A is mounted to the collar 40A, and is provided for engaging one or more complimentary surfaces on the side of the boat 22. When the drive motor 48A is operative to move the belt 44A such that the collar 40A is moved to the left along the shaft 42A, the paddle 38A drags the boat 22 to the left across the base pan 24.

A shaft rotate motor 54A is also provided with an associated belt and pulley (not shown) for rotation of the shaft 42A by an angle of 90 degrees. When the shaft rotate motor 54A rotates the shaft 42A such that the head of the paddle 38A is in a horizontal position in the direction of the boat 22, the paddle 38A is in a position to engage a complimentary surface on the side of the boat 22 so as to drag the boat 22 as the paddle 38A and collar 40A are moved along the shaft 42A. When the boat has reached the end of its travel along the front edge of the base pan 24, the shaft rotate motor 54 rotates the shaft 42A 90 degrees in a direction such that the paddle 38A is rotated upwards away from the side of the boat 22, thereby disengaging the paddle 38A from the boat 22.

Each of the other three drive systems in the sample positioning system 100 is functionally equivalent to the drive system described above for the front edge of the base pan 24, and each is composed of like components. For example, the left hand side LHS drive system has a shaft 42B, collar 40B with attached paddle 38B, drive belt motor 48B, shaft rotation motor 54B etc. Like components for the rear edge of the base pan include a rotatable shaft 42C, belt drive motor 48C, etc. Similarly, right hand side (RHS) drive system has a rotatable shaft 42D, collar 40D and attached paddle 38D, etc.

Dilution station 200

Figure 10:
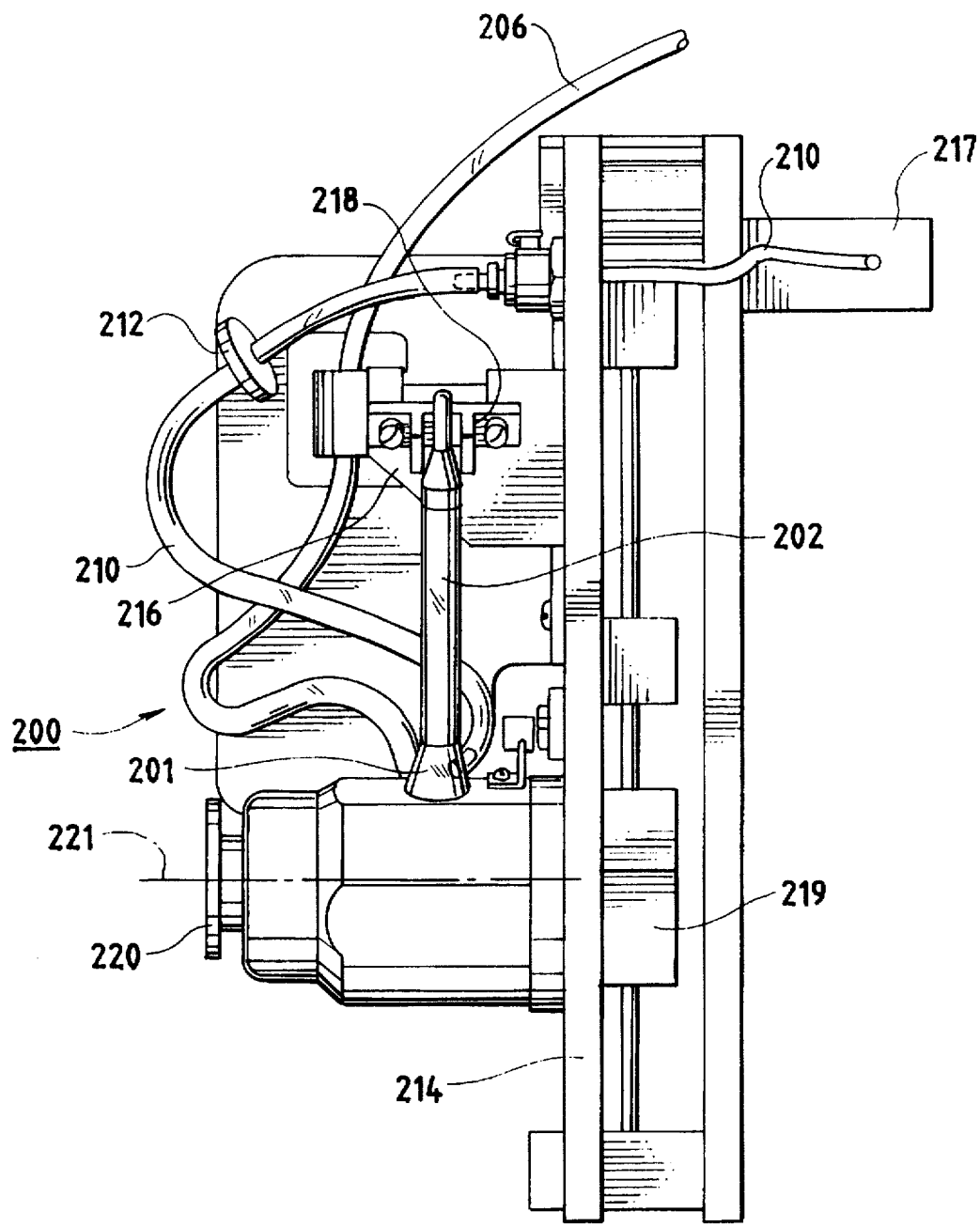
FIG. 10 is a side view of the diluting station of FIG. 9.

The diluting station of FIG. 1 is shown in more detail in FIGS. 8–10. FIG. 8 is perspective view of the diluting and pipetting stations 200 and 300, respectively. FIG. 9 is an elevational view of the stations, and FIG. 10 is a side elevational view of the diluting station 200.

The diluting station 200 can be thought of as a system for dispensing a controlled volume of fluid into a receptacle such as a test tube. The station 200 has a source of diluent fluid 204, such as a flexible bag of saline solution, that rests on a suitable inclined shelf 203. A rotating shot tube 202 having a predetermined volume receives the fluid from the source 204 via a conduit or tube 206. A filter 208 is placed in the conduit 206, and serves to prevent contaminants from entering the line 206.

A solenoid 220 is provided for controlling the opening of a resilient thimble valve placed within the open end 201 of the shot tube 202. The thimble valve controls the flow of the fluid from the conduit 206 into the shot tube 202 by obstructing an intake port for the conduit 206 when the valve is closed, and opening up the port when it is in an open condition. Since the source of fluids 204 is placed above the shot tube 202, the fluid fills the shot tube 202 by gravity flow. The shot tube 202 is mounted to the solenoid 220 housing. The solenoid 220 and attached shot tube is rotatable via a motor 219 (FIG. 10) having a drive belt and pulley (not shown) relative to a bulkhead 214. The motor 219 is placed directly behind the solenoid 202 on the back side of the bulkhead 214.

When the shot tube 202 is rotated to a generally upward orientation (i.e., the tip of the shot tube is elevated with respect to the end 201 of the shot tube), as shown in FIGS. 1, 3 and 4, the shot tube can be filled with fluid such that the shot tube is automatically primed as it is filled. The upward orientation of the shot tube 202 permits air within the shot tube to be eliminated from the shot tube 202 as the fluid enters the end 201 of the shot tube and works its way up to the tip of the shot tube 202. An optical sensor 218 mounted to a bracket 216 is provided for detecting when the diluent fills the shot tube up to the fill zone adjacent to the tip of the shot tube 202.

When the shot tube 202 is filled, the motor 219 behind the bulkhead 214 rotates the solenoid 220 and shot tube 202 in the direction of the arrow 222 (FIG. 9) to a second position, wherein the tip portion of the shot tube 202 is oriented downwardly towards a test tube in the boat 22 (FIG. 1). A second conduit 210 is provided which is in communication with a source of compressed air 217 mounted behind the bulkhead 214. A filter 212 is provided in the conduit 210, and prevents contaminants from entering the line 210. The conduit 210 is fitted over an exhaust tube in the shot tube 202 in the vicinity of the thimble valve. When the shot tube 202 is in the second downward position, compressed air is injected into the shot tube in a stream to exhaust the diluent from the shot tube 202 into the test tube 30B (FIG. 1).

The solenoid 220 drives a piston along a solenoid axis 221, and a cam inside the solenoid couples the piston to a plunger that moves along the axis of the shot tube 202. The plunger has a tip that is received in the interior of the thimble valve. When the plunger is activated to an extended position by the solenoid 220, the tip of the plunger pushes against the central wall of the thimble valve and distorts the shape of the thimble valve, allowing fluids to flow around the edge of the thimble valve into the interior of the shot tube 202. When the solenoid 200 retracts the piston, the thimble valve assumes its normal positon flush against the interior of the shot tube sealing off the fill tube port.

Pipetting station 300

The pipetting station 300 is shown in FIGS. 8 and 9 in an overall aspect. The station 300 includes a pipette hopper 304 and dispensing assembly shown in an end view in FIG. 12 and an exploded view in FIG. 13.

Figure 11:
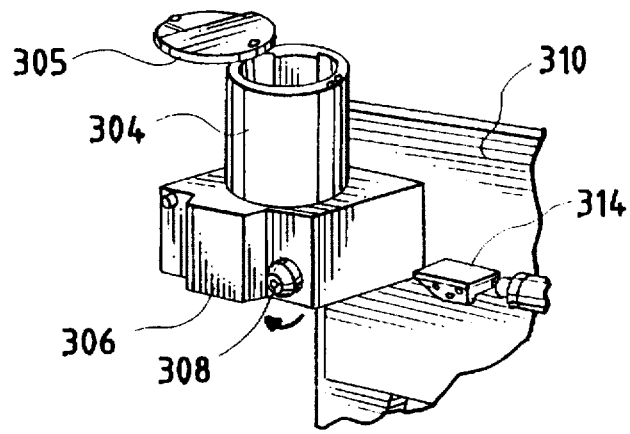
FIG. 11 is a perspective view of the pipetting hopper system of FIGS. 1 and 9 when the pipette housing is rotated to a pipetting fill position, with the cover swung open to permit the housing to be filled with pipettes.
Figure 12:
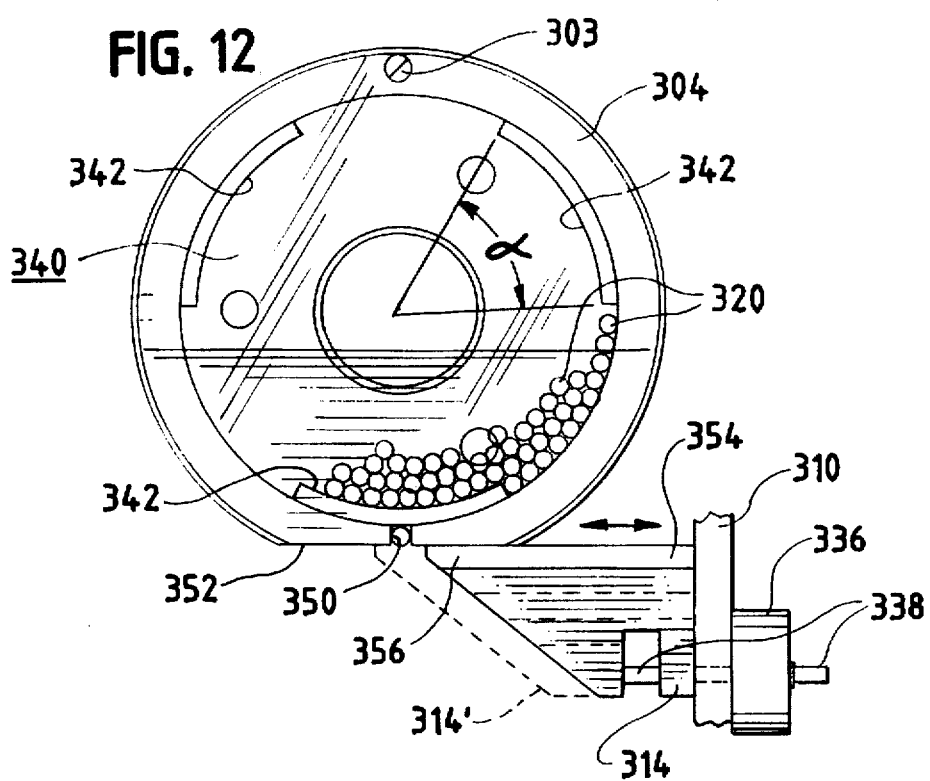
FIG. 12 is an end view of the pipetting hopper system showing the movement of a horizontal slide between two positions, controlling the ability of pipettes to be removed from the housing via a slot in the housing.

Referring to FIGS. 8, 9, and 11-13 in particular, the station 300 includes a generally cylindrical housing or hopper 304 that contains a plurality of hollow pipette straws 320. As seen in FIG. 12, the housing 304 has a horizontally disposed straw withdrawal opening slot 350 at the bottom of the housing 304. The housing 304 is mounted to a block 306 which is rotatable relative to a bulkhead 310 by a pin 308 secured to the bulkhead 310, so as to permit the housing 304 to rotate upwards from the orientation shown in FIG. 1 to the orientation shown in FIG. 11. The housing includes a clear plastic cover 305 which prevents the straws 320 from falling out of the housing 304. The plastic cover 305 is mounted to the housing 304 via a screw 303 and a mounting hole 307 (FIG. 13) in the housing 304. As shown in FIG. 11, the plastic cover 305 swings out from a position covering the housing 304 opening so as to permit a technician to refill the housing 304 with straws 320.

When the housing 304 is in the normal, horizontal position in FIGS. 1 and 12, the slot 350 is positioned immediately above a horizontal slide member 314. Referring to FIG. 12, the horizontal slide 314 has a solenoid 336 that is mounted to the back side of the bulkhead 310 for moving the slide between extended and retracted positions. The solenoid 336 could be mounted to the front of the bulkhead in a different configuration if desired. The movement of the slide 314 is accomplished by moving a shaft 338 that the slide 314 is mounted to back and forth. The slide 314 is slid along guides 337.

A stepping motor 312 (FIGS. 9 and 13) mounted to the rear wall of the drum 340 is provided to sweep a rotatable drum 340 having three equidistantly spaced fingers 342 about the interior surface of the housing 304. In a preferred embodiment, each of the fingers 340 define a sweep angle α of approximately 60 degrees. As best seen in FIG. 12, as the fingers 342 sweep along the interior surface of the housing 304, one of the fingers sweeps a straw 320 in the housing 304 into the slot 350. The fingers 342 stop their movement such that a portion of the finger 342 covers the slot 350, with a straw positioned below the finger in the slot, as shown in FIG. 12. When the horizontal slide 314 is in the position 314' shown in dashed lines in FIG. 12, the top surface 354 of the end portion 356 of the slide 314 is positioned below the slot 350 in contact with a bottom housing surface 352, preventing a straw 320 from falling out of the housing 304 through the slot 350. As shown best in FIG. 12, the sides of the slot 350, the finger 342 and the slide 314 all cooperate to firmly retain the straw 320 in the slot, permitting the tapered tubular transfer pin 330 to be inserted into the end of the straw 320.

Referring to FIG. 12, the housing 304 is made from a low friction material. Preferably, the housing 304 is constructed such that the inside diameter of the housing 304 is less than the length of the housing, so as to maintain the straws 320 in a condition oriented parallel to the length of the housing 304, so that they can be readily swept into the slot 350.

While the slide 314 is in the extended position 314' and the straw is trapped in the slot 350 as shown in FIG. 12, a tapered tubular transfer pin 330 (FIGS. 9, 13) is moved from a retracted position in a transfer pin assembly 316 into an extended position directly into the straw 320 in the slot 350, so as to frictionally engage the tip of the straw 320. At this point, the horizontal slide 314 retracts towards the bulkhead 310. The transfer pin 330 now is rotated by a motor 360 (FIGS. 14-16) to a vertical position as shown in FIG. 1, permitting the straw 320 to be moved through the slot 350 out of the housing 304. As soon as the straw 320 is rotated out of the slot 350, the slide 314 is moved back to the position 314' shown in dashed lines in FIG. 12, and the motor 312 is operated to sweep another straw 320 into the slot 350.

The tapered tubular transfer pin 330 with attached straw 302, now in a vertical orientation directly above one of the test tubes in the cassette 26, is lowered so that the end of the straw 302 (FIG. 1) is immersed sufficiently into the fluid in one of the test tubes (e.g. test tube 30A), such as a test tube containing a biological or control fluid sample. Vacuum is applied to the tubular transfer pin 330 and attached straw 302 for a predetermined period of time, drawing a precise and controlled volume of fluid into the straw 302. The tubular transfer pin 330 and attached straw (with fluid) is raised up so as to clear the top of the test tube. The boat and test tube are advanced by the positioning system 100 by an amount equal to the separation distance of adjacent test tubes. The tubular transfer pin 330 and straw 302 are lowered into the susceptibility test tube 30B, whereupon the vacuum applied to the transfer pin 330 is released, causing the fluid contents of the straw 302 to fall into the susceptibility test tube 30B. At this point, the tubular transfer pin 330 is moved to a position wholly within the tubular transfer pin housing so as to eject the straw 302, dropping the straw in the susceptibility test tube. The transfer pin assembly 316 is then raised back to the elevation of the hopper 304, rotated into a horizontal position, and the process repeated.

Figure 14:
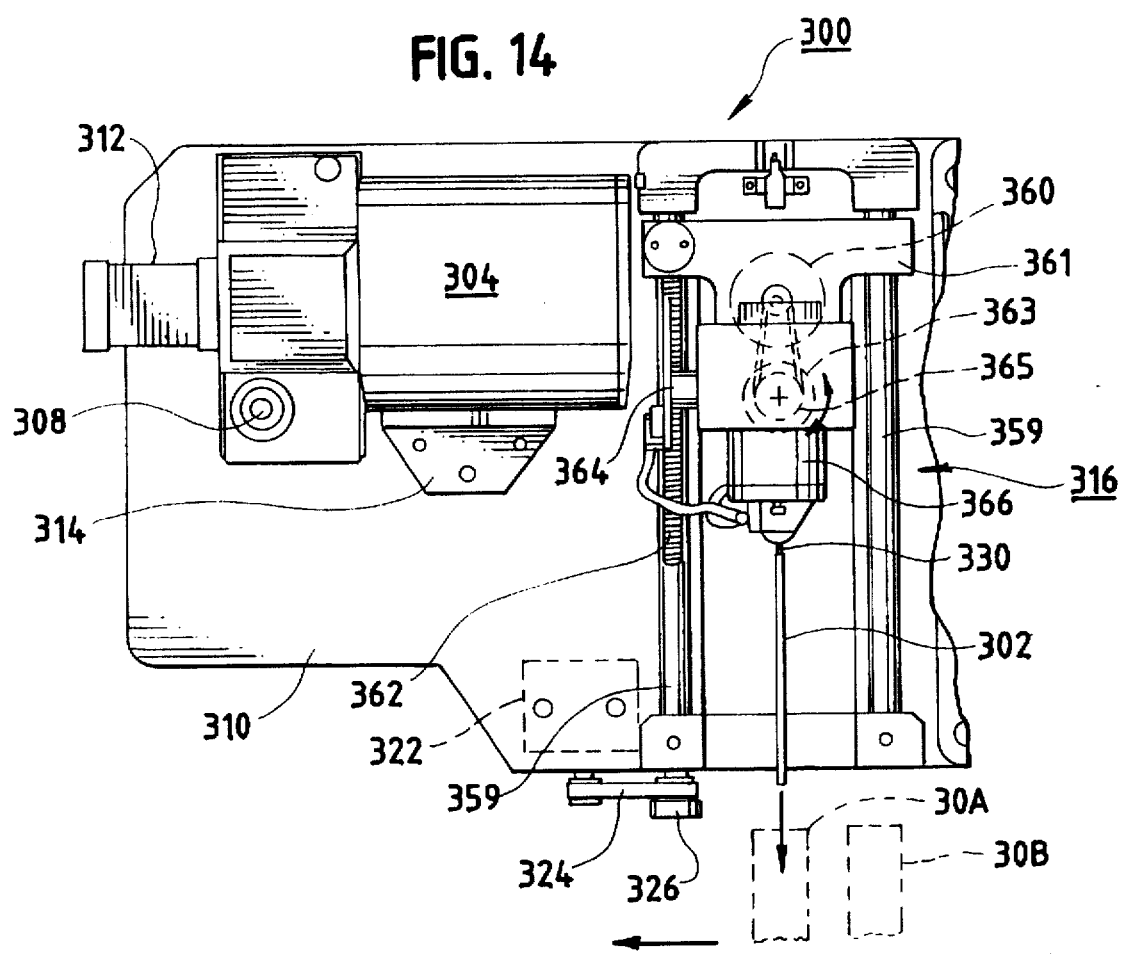
FIG. 14 is an elevational view of the pipetting station 300 of FIG. 1, with the tubular tapered transfer pin assembly rotated to a fluid withdrawal position where the straw can be lowered into a receptacle.
Figure 15:
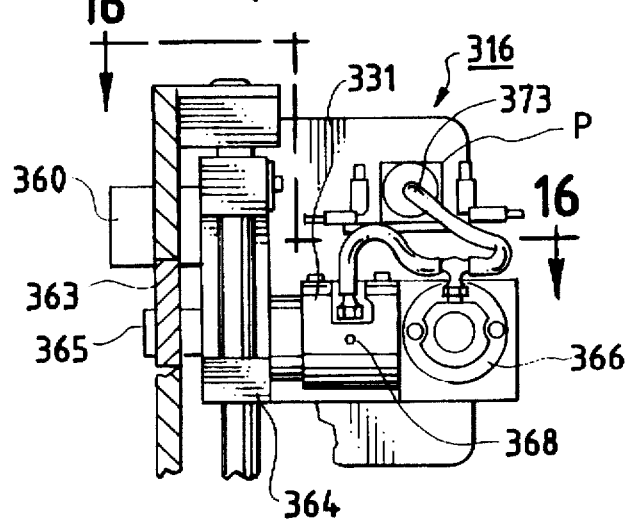
FIG. 15 is a side view of the tubular tapered transfer pin assembly as seen from the straw hopper of FIG. 14.
Figure 16:
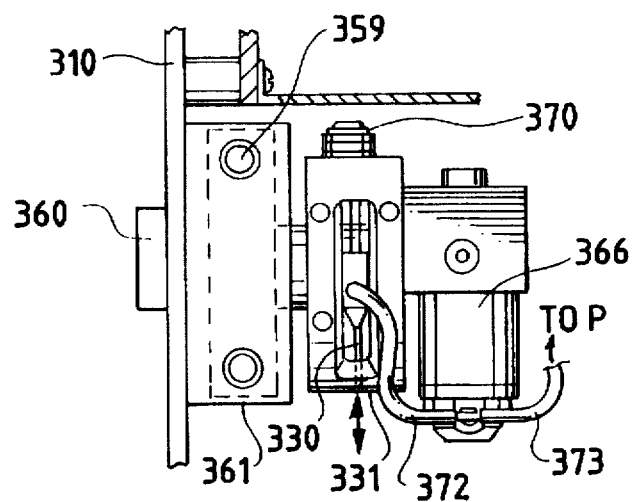
FIG. 16 is a top plan view of the tubular tapered transfer pin assembly along the lines 16—16 of FIG. 15.

Referring to FIGS. 14, 15 and 16, the transfer pin assembly 316 and associated motor and vacuum system for the transfer pin 330 are illustrated in greater detail. Referring to FIG. 14 in particular, a motor 322 is mounted behind the bulkhead and includes a drive belt 324 that turns a pulley 326 and a threaded shaft 362, referred to in the art as an ACME thread or lead screw. A transfer pin plate 361 is mounted to the threaded shaft via a pair of collars 364. Depending on the direction that the motor 322 rotates the shaft 362, the plate 361 and attached transfer pin assembly 316 is slid either up or down the two pillars 359 between an upper position, in which the transfer pin 330 is at the same elevation as the straw withdrawal slot 350 in the housing 304, and a lower position in which the straw 302 is in a position to withdraw fluid from a receptacle placed below the transfer pin assembly 316.

A second motor 360 having a drive belt 363 and pulley 365 is mounted to the rear of the transfer pin plate 361, and is provided for rotation of the entire transfer pin assembly 316 in the direction of the arrow of FIG. 14 between a first position, in which the transfer pin 330 is oriented in the direction of the straw withdrawal slot 350, to a second position, in which the straw 302 is oriented vertically downward in the position shown in FIGS. 1 and 14.

Figure 13:
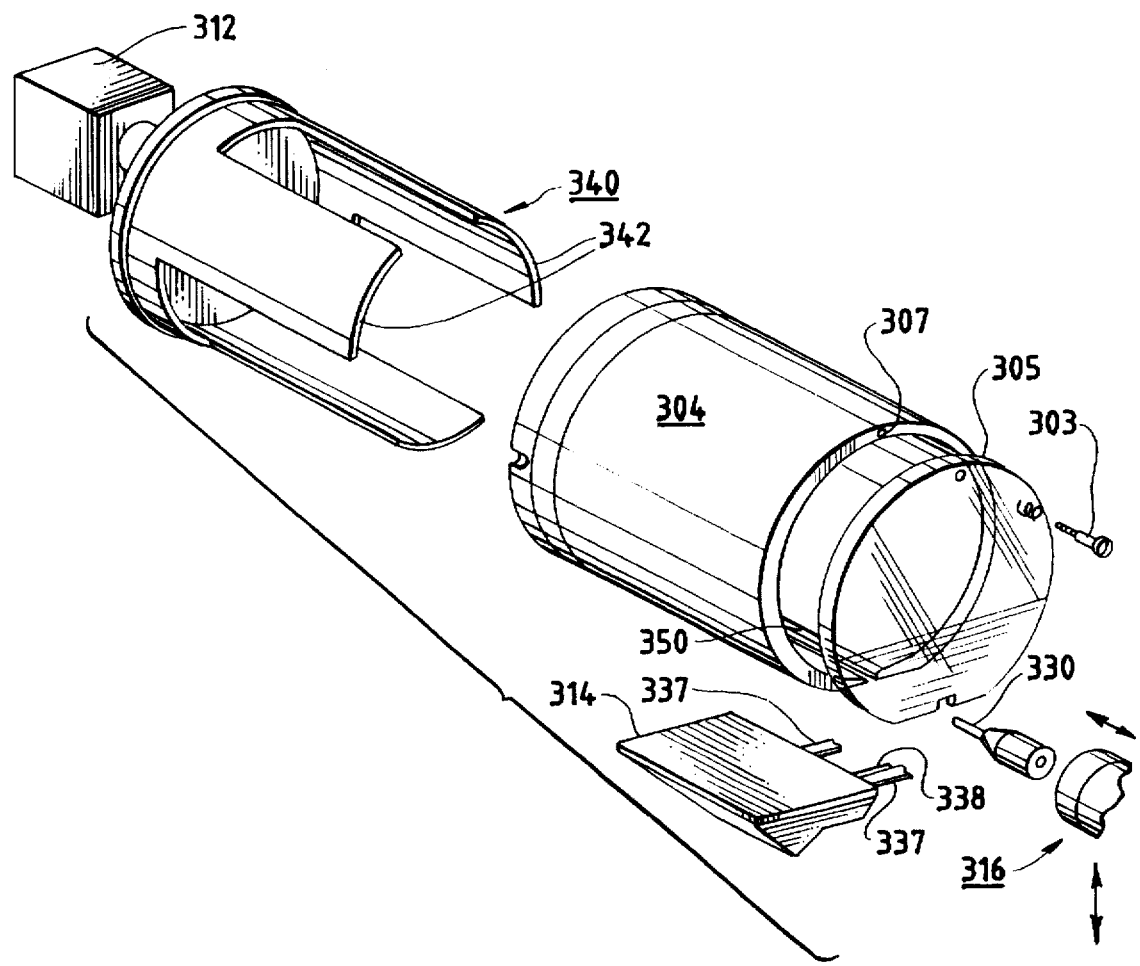
FIG. 13 is an exploded view of the pipette hopper system of FIGS. 10 and 11.

Referring to FIG. 15, the transfer pin assembly 316 is illustrated in a side view as seen from the pipette housing 304. The transfer pin assembly has a transfer pin housing 331 which defines a transfer pin aperture 368. The tapered tubular transfer pin 330 (FIG. 16) reciprocates between a retracted position in the housing (shown in FIGS. 15 and 16), and an extended position shown in FIG. 14 at which it engages a straw in the straw withdrawal slot 350 as shown in FIG. 13. A transfer pin actuation solenoid 370 is mounted to the rear of the transfer pin assembly 316 to move the tubular tapered transfer pin 330 between the retracted and extended positions. A source of vacuum 366 is mounted adjacent to the transfer pin housing 331, and provides vacuum to the end of the transfer pin 330 via a tube 372. A vacuum pressure transducer P is provided which monitors the vacuum generated by the source 366 to ensure that a straw is attached to the tapered tubular transfer pin 330, that fluid is withdrawn into the straw, and that a sufficient volume of liquid is transferred. This pressure transducer P is positioned at the end of a secondary vacuum line 373 in communication with the vacuum source. A suitable pressure transducer P is the Motorola model MPX 5010D sensor.

When the transfer pin 330 and straw 302 are rotated from a horizontal position to the vertical position shown in FIG. 14, the straw 302 is rotated out of the slot 350 in the housing 304. The motor 322 then operates to lower the transfer pin assembly 316 to the appropriate level such that the straw 302 is immersed in the test tube 30A. After withdrawal of the fluid from the test tube 30A, the motor 322 raises the transfer pin assembly 316 up such that straw 302 clears the top of the test tube 30A, and then lowers the assembly 316 into test tube 30B after test tube 30B is placed below the straw 302. To remove the straw 302, the transfer tube 330 is retracted into the transfer tube housing 331. The diameter of the straw 302 is slightly larger than the diameter of the transfer pin aperture 368, forcing the straw 302 off of the transfer pin 330 as the transfer pin 330 with completely withdrawn into the transfer pin housing 331 in the position shown in FIG. 16. In this embodiment, the straw 302 falls into test tube 30B. The transfer pin assembly is then rotated back into a horizontal position and raised to the level of the straw withdrawal slot 350 in the housing 304, and the process is repeated for the next set of test tubes.

Vacuum Control of Card Loading

Figure 29:
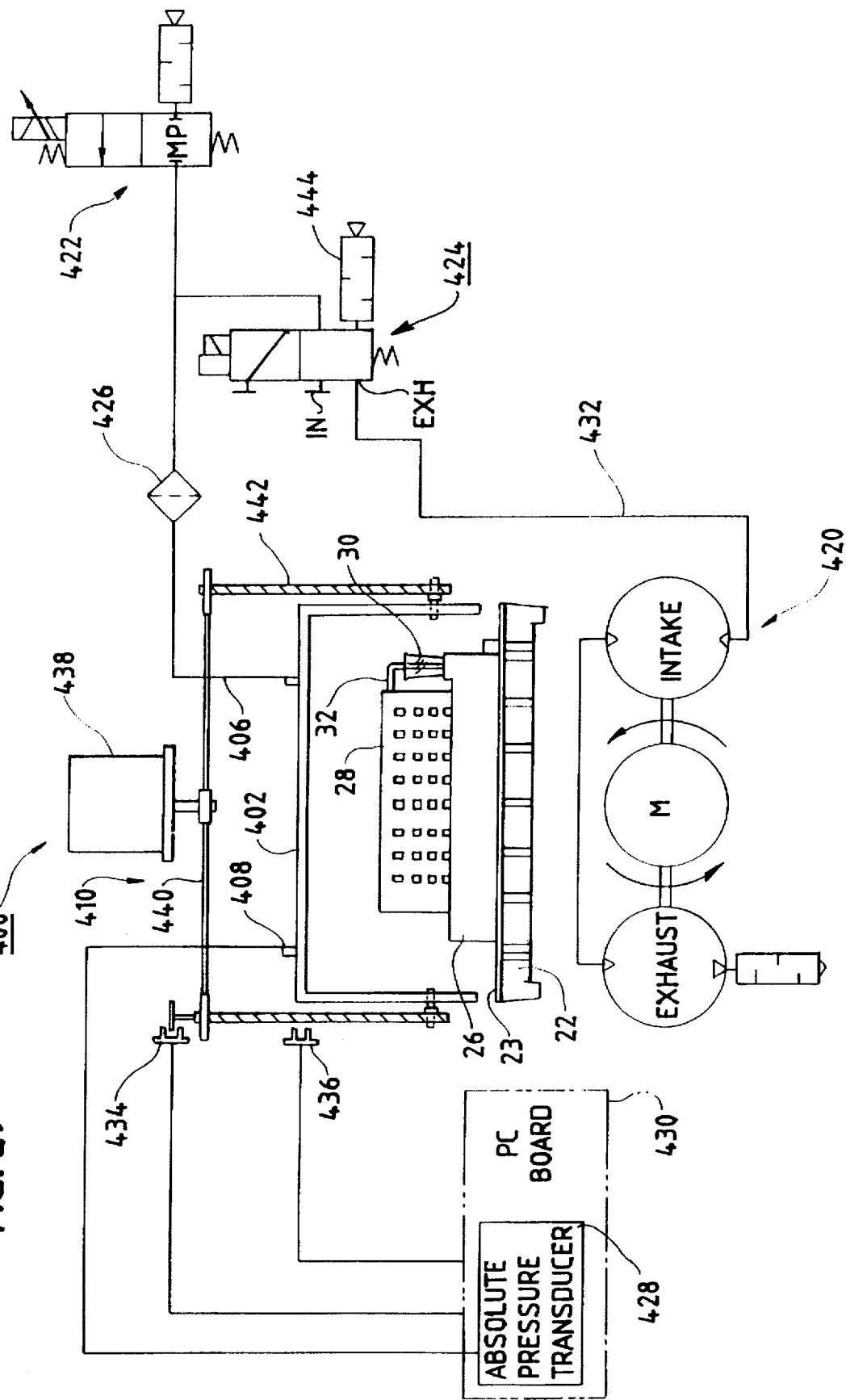
FIG. 29 is a schematic diagram of the vacuum station of FIG. 3.

At the vacuum station 400, the vacuum loading of the cards 28 in the vacuum chamber 402 is controlled in a manner to prevent the formation of bubbles in the wells of the cards 28. The station 400 is shown schematically in FIG. 29.

The vacuum filing station 400 consists of the following components:

A vacuum pump 420 (Gast P/N: SAA-V110-NB, 115 VAC, 50/60 Hz, 29.5 inch Hg max. Vacuum: 1.75 cfm open flow).

A proportional vacuum control valve 422 (Honeywell/Skinner P/N: BP2EV0006, 12–24 VDC, 0–5 VDC Control, 0.078 inch diameter orifice).

A 4-way direct acting solenoid valve 424 (Humphrey P/N: 420 24 VDC, 60 scfm @ 1100 PSIG inlet pressure, 24 VDC, 0.250 inch diameter orifice).

An air filter 426 (Norgren P/N: F39-222EOTA, 4 scfm @ 100 PSIG inlet pressure, 0.01 micron filtration).

An absolute pressure transducer 428 (Dara Instruments P/N: XCA415AN, Range: 0–15 PSIA, 5 VDC Excitation, 0.25–4.25 V F.S.O., ±0.5% of F.S.O. Combined Linearity & Hysteresis, ±0.3% of F.S.O. Repeatability).

A standard sample preparation node (SPN) printed circuit board 430.

Vacuum tubing 432, 0.250 inch inside diameter.

The drive system 410 for the station 400 includes a stepping motor 438 and associated belts 440 and threaded shafts 442 that raise and lower the vacuum chamber 402. An optical encoder 434 and optical interrupt 436 sense when the vacuum chamber 402 is at its upper and lower positions, respectively.

When the vacuum pump 420 is turned on, it pulls free air through the filter/muffler 444 attached to the 4-way solenoid valve 424. To fill the card 28 in the boat 22, the following sequence occurs: The vacuum chamber 402 is lowered onto the boat 22 with the sample cards 28. The proportional and vacuum control valve 422 is opened 100%. The 4-way solenoid valve 424 is energized and air is pumped out of the vacuum chamber 402 through the air filter 426 and the 4-way solenoid valve 424. The absolute pressure transducer 428 gauges the vacuum chamber 402 pressure decrease and sends a proportional continuously changing voltage output to the SPN Board 430. The continuously changing voltage is sampled by the SPN Board 430 at regular intervals and the rate of change is compared to the programmed rate to pump down the vacuum chamber.

If the rate of change is too fast, the proportional valve 422 is sent a higher control voltage to open wider, if possible, and increase the size of the air leak into the vacuum line 406. If the rate of changes is too slow, the proportional valve 422 is sent a lower control voltage to close down, if possible, and decrease the size of the air leak into the vacuum line 406. The control of the rate of change of pressure insures that vacuum is not drawn too quickly, which can cause splashing and bubbles in the test tubes 30. This can cause air bubbles to enter the card 28 when the chamber is vented, interfering with the optical analysis of the card.

The absolute pressure transducer 428 continues to gauge the vacuum chamber 402 pressure and send the proportional pressure voltage to the SPN Board 430 while the 4-way solenoid valve 424 is deenergized. The vacuum pump 420 is turned off, and the proportional valve 422 is closed completely for five seconds when the vacuum target (or set point) pressure of 0.90 PSIA is reached. This is to prevent the possibility of the pressure in the vacuum chamber from varying up and down enough to allow sample fluid to be transported in and out of the test card 28 during the five second dwell period.

The absolute pressure transducer 428 continues to gauge the vacuum chamber 402 pressure and send the proportional pressure voltage to the SPN board 430, while the proportional valve 422 is opened gradually at the end of the five second vacuum dwell period until the programmed pressure increase rate of change is achieved.

The continuously changing voltage from the pressure transducer 428 is sampled by the SPN Board 430 at regular intervals and the rate of change to return to atmospheric pressure is compared to the predetermined programmed rate. If the rate of change is too fast, the proportional valve 422 is sent a lower control voltage to close down, if possible, and decrease the size of the air leak into the vacuum line 406. If the rate of change is too slow, the proportional valve 422 is sent a higher control voltage to open wider, if possible, and increase the size of the air leak into the vacuum line 406. This steady controlled venting permits fluid samples to be drawn into the sample cards 28 in a manner to reduce the risk of bubbles forming in the wells of the card 28, and to insure complete filling of the card 28.

The proportional valve 422 is opened 100% at the complete return to atmospheric pressure and held open while the vacuum chamber 402 is raised from the boat 22. This is to prevent a residual vacuum from occurring in the chamber 402 and lifting the boat 22 within the chamber 402. The proportion valve is closed and the system is ready to repeat the cycle.

Figure 30:
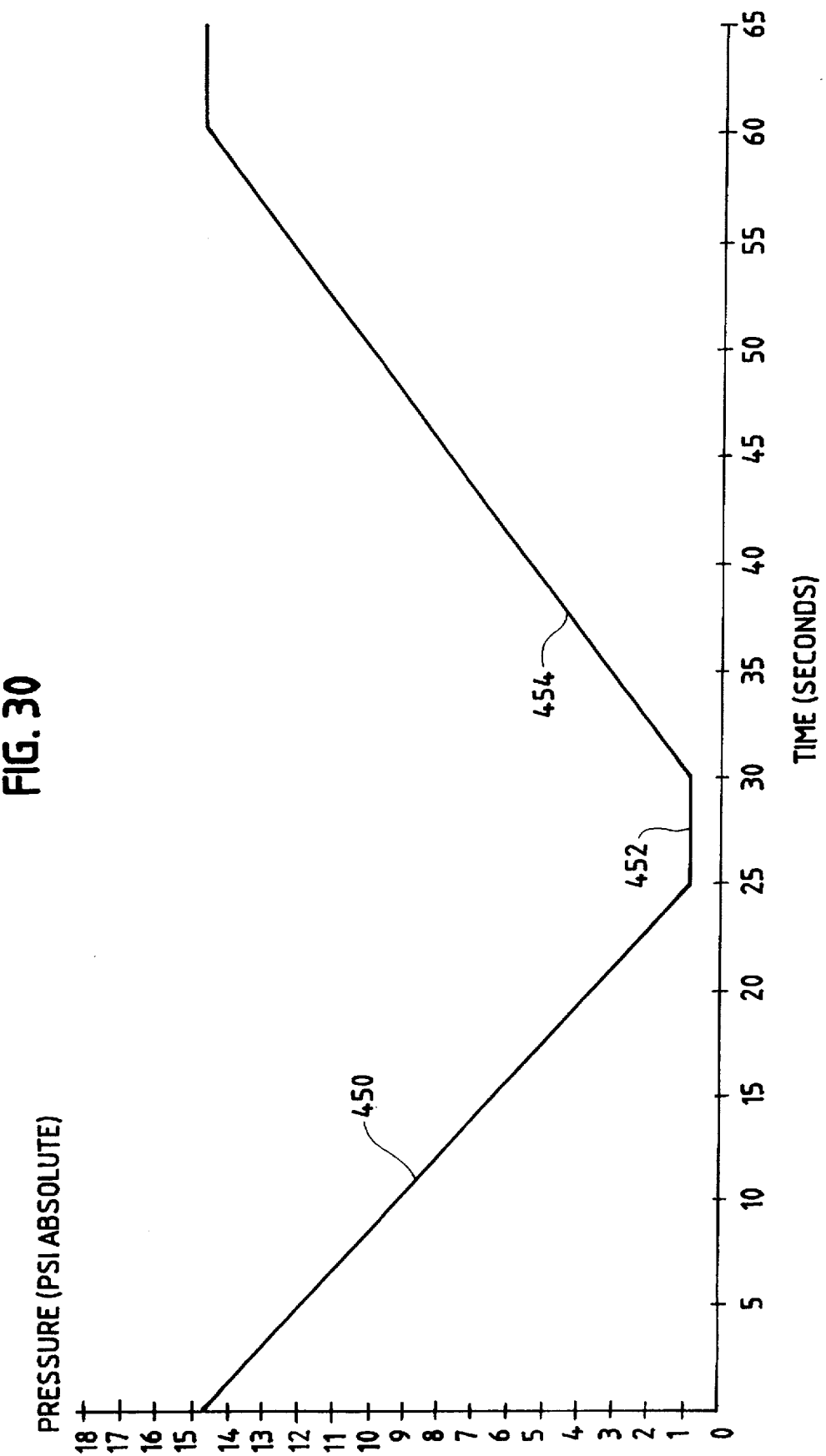
FIG. 30 is a graph of showing the change in vacuum inside the vacuum chamber of FIG. 29 as a function of time during the loading of the cards.

The vacuum generation, dwell, and venting cycle is illustrated in graphical form in FIG. 30. Note the linear draw down curve 450 of about −0.54±0.07 PSIA per second, the 5 second dwell period 452 at 0.90 PSIA, and the linear vent rate curbe 454 of about +0.45±0.07 PSIA per second.

For the illustrated embodiment, it is assumed the relative pressure between the test card 28 and the surrounding atmospheric media inside the vacuum chamber 402 to be 0 PSI. In reality, there should be a very small pressure difference inside the test card 28 versus outside the test card 28 in the vacuum chamber throughout the filling cycle. If, however, one considers the pressure changes inside versus outside the vacuum chamber, then the following cycle information applies to the illustrated embodiment: Initial: local atmospheric pressure (varies with local barometric pressure). Start filling cycle: −0.53±0.07 PSI/sec (23–30 seconds pump down). Vacuum dwell: Approx. 5 seconds. Return to atmospheric pressure: +0.53±0.07 PSI/sec (23–30 seconds return). A return to atmospheric rates faster than this can causes some test card fills to be incomplete. End: Local Atmospheric Pressure (same as initial).

Transfer Tube Cut and Seal Station 500

Once the card is filled with sample in the vacuum chamber 402, the cassette 26 is moved through a transfer tube cutting and sealing station 500, best seen in FIGS. 1, 4, and 5. A formed nichrome wire 506 is heated to a precise temperature for cutting through the transfer tubes 30 using a microprocessor-controlled constant current source (not shown).

The cassette 26 is moved past the hot wire 506 at a slow speed to allow the wire to cut and seal the transfer tubes 30 close to the card 28, forming an external transfer stub. The remainder of the transfer tube 30 remnant is left in the test tube for disposal, as shown in the extreme right hand side of the boat 22 in FIG. 5.

The hot cutting wire 506 is mounted to a mechanism including plates 504 that are raised and lowered by a stepper motor/pulley/drive belt drive assembly 502 (FIG. 1), allowing the wire 506 to be moved out of the way to allow un-cut transfer tubes to be moved past the cutting and sealing station 500. This function can be used to batch load multiple cassettes or for error recovery purposes.

The cutting and sealing station 500, in cooperation with the test sample positioning system 100, enables multiple transfer tubes to be cut essentially at once as the boat 22 is advanced past the hot cutting wire 506. Control of the cutting of the transfer tube to produce a reliable seal is accomplished by using a constant current source to control the heat output of the hot cutting wire 506, and controlling the speed at which the boat 22 and cassette 26 is moved past the wire 506. Since the electrical properties of the wire 506 are predetermined, and by holding the current constant and controlling the speed at which the wire passes through the plastic transfer tube 30 (i.e., the speed of motor 48C), the station 500 can simply and precisely control the cutting and sealing of the transfer tube 30. This heat control design is very simple and does not need temperature calibration. The wire 506 heats up very quickly, so the wire does not have to be left on all the time. This feature offers safety and energy conservation advantages.

In the prior art cutting and sealing station of the Vitek® sealer, a block of metal is with a cartridge heater embedded with a thermocouple connected to a conventional temperature control. This is a fairly expensive, bulky device that needs calibration, cuts only one straw at a time, and requires a long, constantly "ON" heating time. In contrast, the present inventive sealing station 500 is much smaller, more reliable, and less expensive to manufacture. Rather than controlling temperature, as in the prior art, the station 500 controls the power with a constant current source applied to the cutting/sealing wire 506 to control heat. Heat is a function of the square of the current since power $(P)=I^2R$. Typically, the setting for the constant current source is set at the factory once and would not have to be adjusted in the field.

Optical Scanner Transport Station 700

Figure 17:
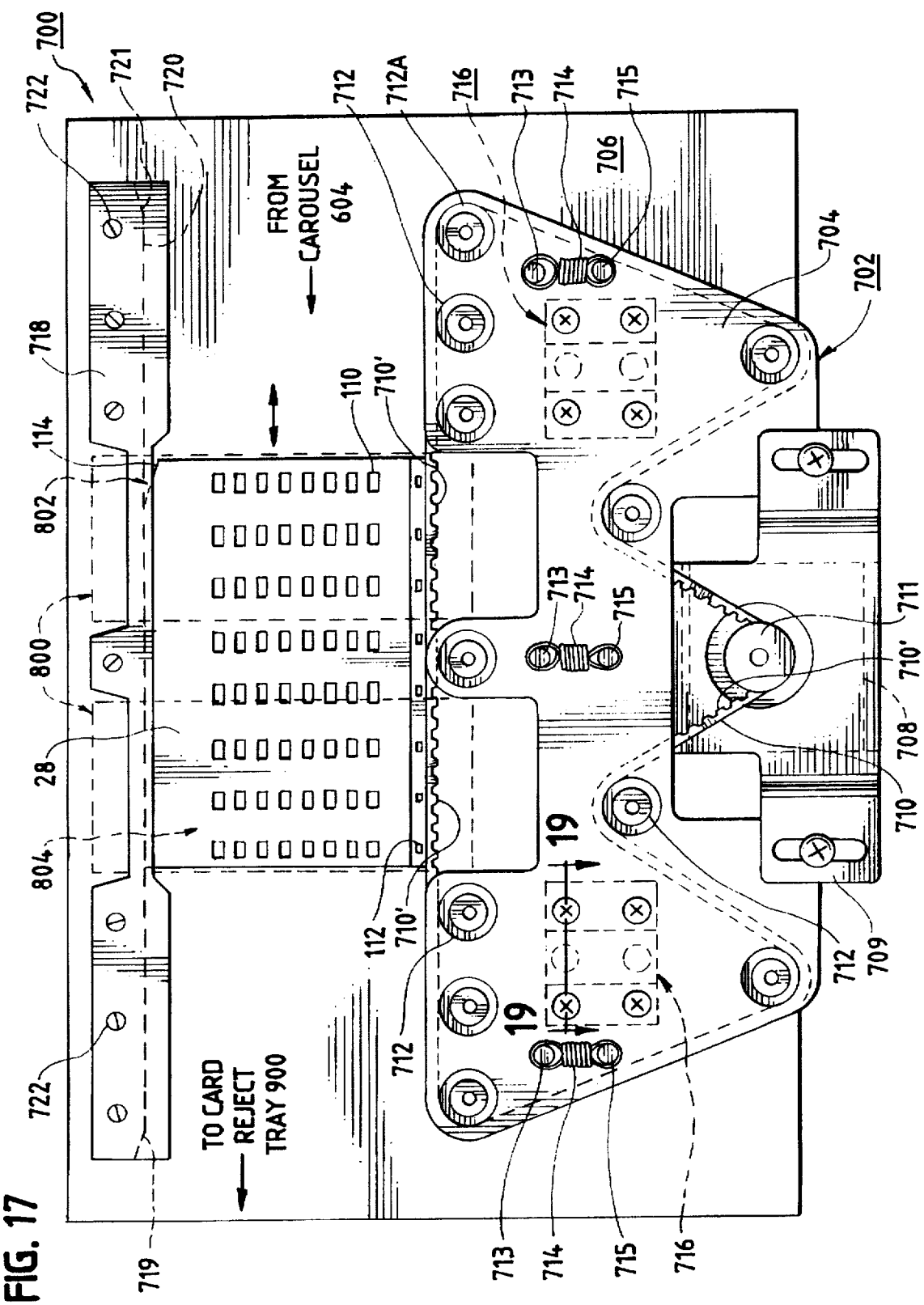
FIG. 17 is a plan view of a preferred sample card transport system for the machine of FIGS. 1 and 2.

Referring now to FIG. 17, the sample card transport station 700 for the optical scanners is shown in an elevational view. The station 700 includes a drive assembly 702 having a cover plate 704 which is mounted to a bulkhead or support 706. The optical reader system 800 in the preferred embodiment consists of a transmittance substation 802 and a fluorescence substation 804 mounted to the bulkhead 706, the outlines of which are shown in FIG. 17. The sample card 28 is moved from the top of the carousel 604 by the drive assembly 702 through the optical reader system 800 and back to the carousel 604 if the card 28 needs further incubation and additional reading. If the card has been sufficiently incubated (based on the analysis of data from the optical reader system 800), the card 28 is moved to a card reject tray 902 (FIGS. 2 and 3) to the left of the optical system 800.

The drive assembly 702 consists of a stepper motor 708, shown in dashed lines, positioned behind a mounting bracket 709. The motor 708 drives a timing pulley 711 that moves an endless, substantially inelastic, drive belt 710 having teeth 710 over a series of rollers 712. The belt 710 is supported at the top of the cover plate 704 by a set of rollers 712. The path of the belt through the rollers 712 is shown in dashed lines in FIG. 17. It can be seen that the belt 710 passes across the top of the cover plate 704 and beneath the optics in the optical substations 802 and 804. The drive belt 710 engages the bottom edge of the card 28 along the top of the cover plate 704. A suitable drive belt 710 can be obtained from the Gates Rubber Co., of Denver, Colo.

Figure 19:
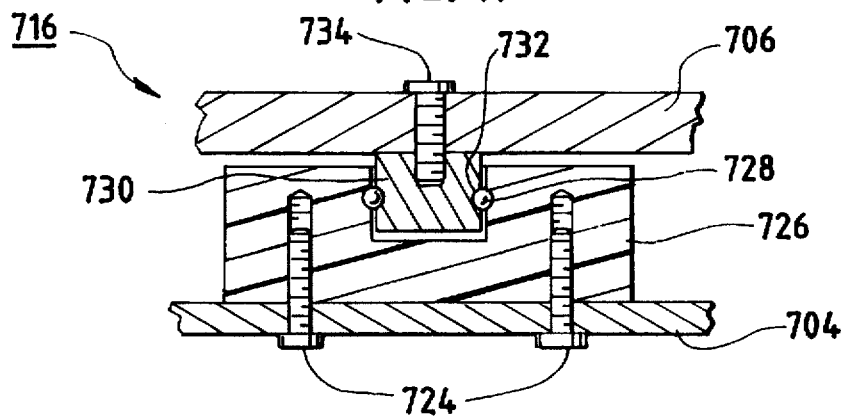
FIG. 19 is a side view of the sample card transport station of FIG. 17, looking in the direction of the carousel and incubation station of FIGS. 1 and 2.

A ledge 718 mounted to the bulkhead 706 is provided above the belt 710 and the optical reading system 800. The ledge has a slot 720 which receives the upper edge of the card 28. The ledge 718 and slot 720 defines a card travel direction. When the card 28 is pushed out of the carousel 604, the card 28 is snugly positioned in the space between the slot 720 and the belt 710. The entire drive assembly 702, including cover plate 704, stepper motor 708 and drive belt 710, is movable relative to the support bulkhead 706. To permit the relative movement, a set of carriage and slide assemblies 716 are provided, one of which is shown in more detail in FIG. 19. As seen in FIG. 19, each of the carriage and slide assembly 716 includes a slide 730 mounted to the bulkhead 706 by a bolt 734. The carriage 726 is mounted to the cover plate 704 by a set of four screws 724. The carriage 726 slides relative to the slide member 730 by means of ball bearings 728 which slide along a groove 732. In the preferred embodiment, two of the carriage and slide assemblies 716 are provided, one on each side of the cover plate 704.

The entire drive assembly 702 is biased upwards towards the ledge 718 by biasing springs 714. The springs have a top end 713 engaging a pin mounted to the bulkhead 706, and a bottom end 715 engaging a pin mounted to the cover plate 704. Three springs 714 in all are preferred, and are placed at the center and sides of the cover plate 704. The springs 714 each have a spring constant K of 16.5 lbs/in., for a total of 49.5 lbs/in for the three springs. The purpose of the springs 714 is to constantly maintain the proper upward pressure on the card 28 by the belt 710, such as in the case of some tolerance variation in the height of the cards. The drive belt 710 must provide enough upward force so as to permit the belt to engage the bottom of the card 28 and move the card along the slot 720, but not too much to cause binding by the drive motor or too little force, which would cause the belt to slip relative to the bottom of the card. By maintaining the proper upward force on the card, such that belt travel is directly translated into card travel, precise movement by the stepper motor 708 results in precise movement of the card 28 relative to the optical system 800. This precise movement is discussed in greater detail in conjunction with the operation of the transmittance substation 802.

Figure 18:
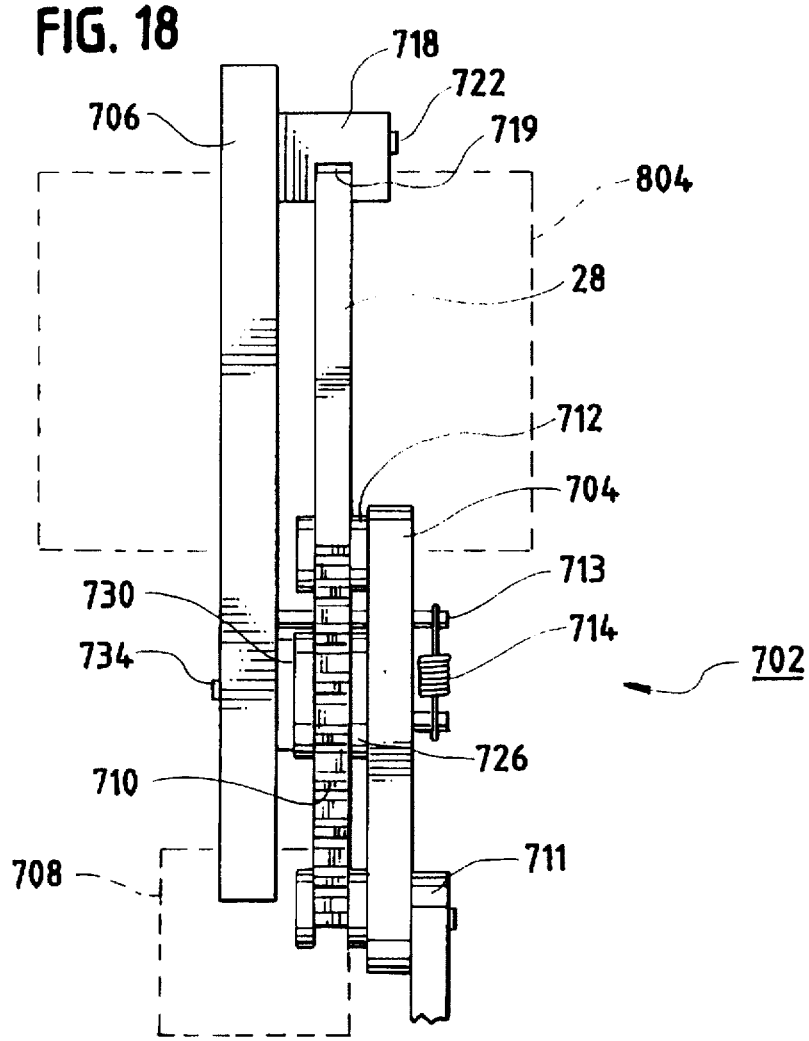
FIG. 18 is a sectional view of the carriage and slide assembly of FIG. 17, which permits the drive subassembly to move relative to the bulkhead.

Referring to FIG. 18, the drive assembly 702 and bulkhead 706 are shown in a side view, looking towards the carousel 604 and incubation station 600 of FIG. 17. The rollers 712 at the top of the cover plate 704 form a slot, as shown, which helps support the bottom edge of the card 28. The card 28 is snugly positioned between the belt 710 and the slot 720 in the ledge 718. The upward force on the card 28 by the springs 714 causes the belt 710 to grip the bottom edge of the card 28, such that the card 28 is slid along the ledge 718 by the drive belt 710 without any significant slippage between the belt 710 and the card 28. To facilitate the sliding motion, the slot 720 is made from a low friction material such as Delrin or given a low friction coating. The bottom edge of the card 28 can be provided with a knurled texture surface such as parallel raised ridges to better enable the belt 710 to grip the card 28 as the belt 710 moves backward and forwards over the rollers 712.

When the leading edge of the card 28 reaches the transmittance substation 802, an optical interrupt LED in the transmittance substation transmits radiation through an optical interrupt aperture 112 at the base of the card 28. An optical interrupt detector senses the radiation and sends a signal to the control system to cause the motor 708 to stop. When the motor 708 stops, the first column of wells 110 in the card 28 are positioned directly opposite a set of eight transmittance LEDs in the transmittance substation 802, which conduct transmittance testing of the column of wells in the card 28.

After an initial illumination of the LEDs, the motor 708 is operated to rapidly move the belt 710 in a series of small steps, such that the transmittance optics luminates the individual wells at a series of positions across the width of the wells. This precise movement of the cards 28 achieves a large set of data for the wells 110. The transmittance testing at multiple positions across the wells 110 will likely include a detection of any air pockets or debris in the wells, enabling the data processing system to detect and possibly reject an abnormal transmittance measurement.

Where fluorescence testing is called for, after all of the wells of the card 28 have been subject to the transmittance testing by transmittance substation 802, the motor 708 and belt 710 slides the card 28 to the fluorescence substation 804, wherein fluorescence testing of the wells 110 takes place.

Depending on the test status, the card 28 is then either returned to the carousel 604 by moving the motor 708 and belt 710 in the reverse direction, or else the motor 708 and belt 710 are operated to move the card all the way to the left hand edge of the drive assembly 702 to place the card 28 in the card disposal mechanism 900.

Fluorescence Optics Substation 804

Figure 20:
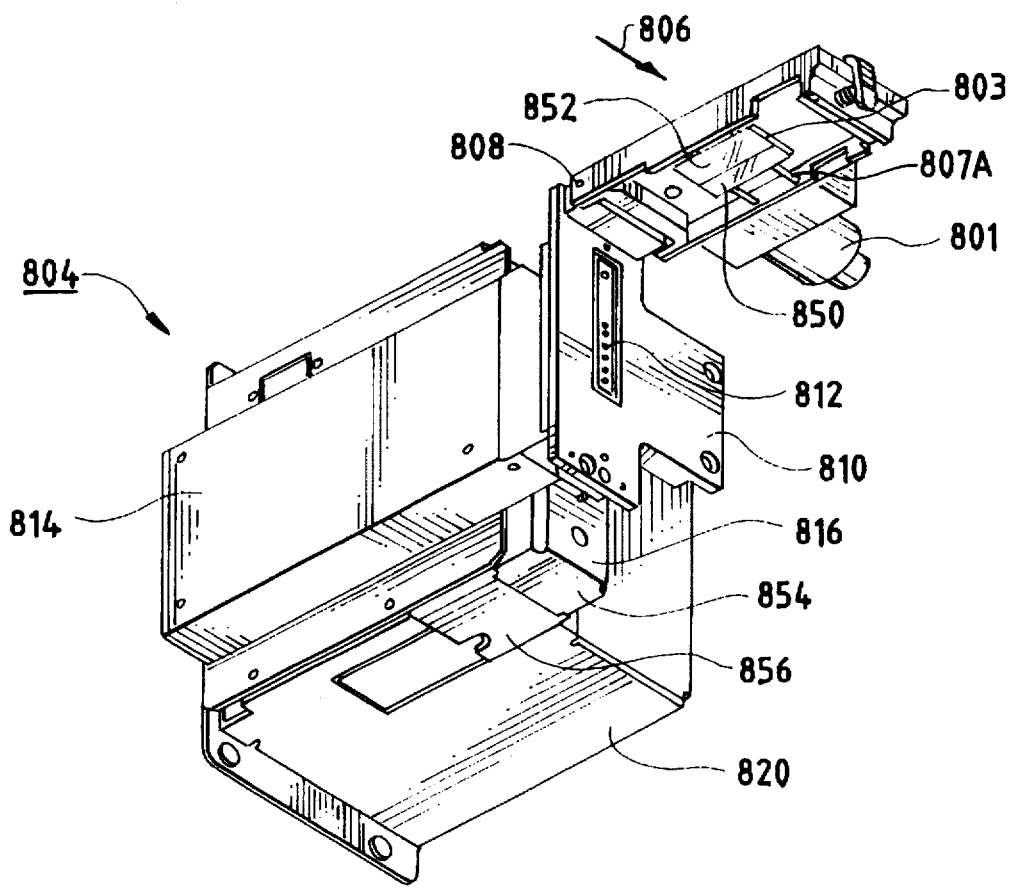
FIG. 20 is a perspective view of the fluorescence optical substation of the optical reading system of FIGS. 1 and 2, with the reflector assembly in an open position to better illustrate the optical head and the optical shuttle.

Referring now to FIG. 20, the fluorescence optics substation 804 is shown in a perspective view isolated from the machine 20. The substation 804 includes a reflector assembly 806 mounted via a hinge 808 to an optical head 810. The optical head 810 has a plurality of surface apertures 812 defining six optical channels between a fluorescence illumination source and the middle six wells in a column of wells in the card 28. The illumination source is placed within a flashlamp cassette 816.

When the hinge 808 is in a closed condition, the reflector assembly 806 is positioned parallel to the apertures 812. The card 28 is moved back and forth in the space defined by the front surface apertures 812 and the reflector assembly 806. An LED and detector cooperate with the optical interrupt aperture 112 along the base of the card 28 to precisely position the card in the space between the front surface aperatures and the reflector assembly.

The reflector assembly 806 has a stepper motor 801 which moves an optical shuttle 803 back and forth along guides 807. A reflector 852 and a solid reference 850 are mounted to the optical shuttle 803. The purpose of the reflector and solid reference are described in more detail below. In normal operation, the shuttle 803 is in a position such that the reflector 852 is placed directly opposite the apertures 812 of the optical head 810. Whenever a calibration of the detectors in the optical head 810 is performed, the motor 801 moves the shuttle 803 such that the solid reference 850 is placed in the optical path opposite the apertures 812. The reflector assembly housing includes a housing for an LED for the optical interrupt aperture 112 for the card 28. A spring clamp 805 is provided to secure the reflective assembly to the head 810 when the assembly 806 is in a closed condition.

Referring again to FIG. 20, the flash lamp cassette 816 holds an elongate xenon linear flash lamp, which serves as a fluorescence illumination source for the fluorophores placed in the wells 110 of the card 28. The flash lamp cassette 816 is connected to a high voltage power supply 820. A peak detector 814 and electronics module is mounted behind the optical head 810. The flash lamp cassette 816 includes a interface block 854 and a lamp holder 856.

Figure 21:
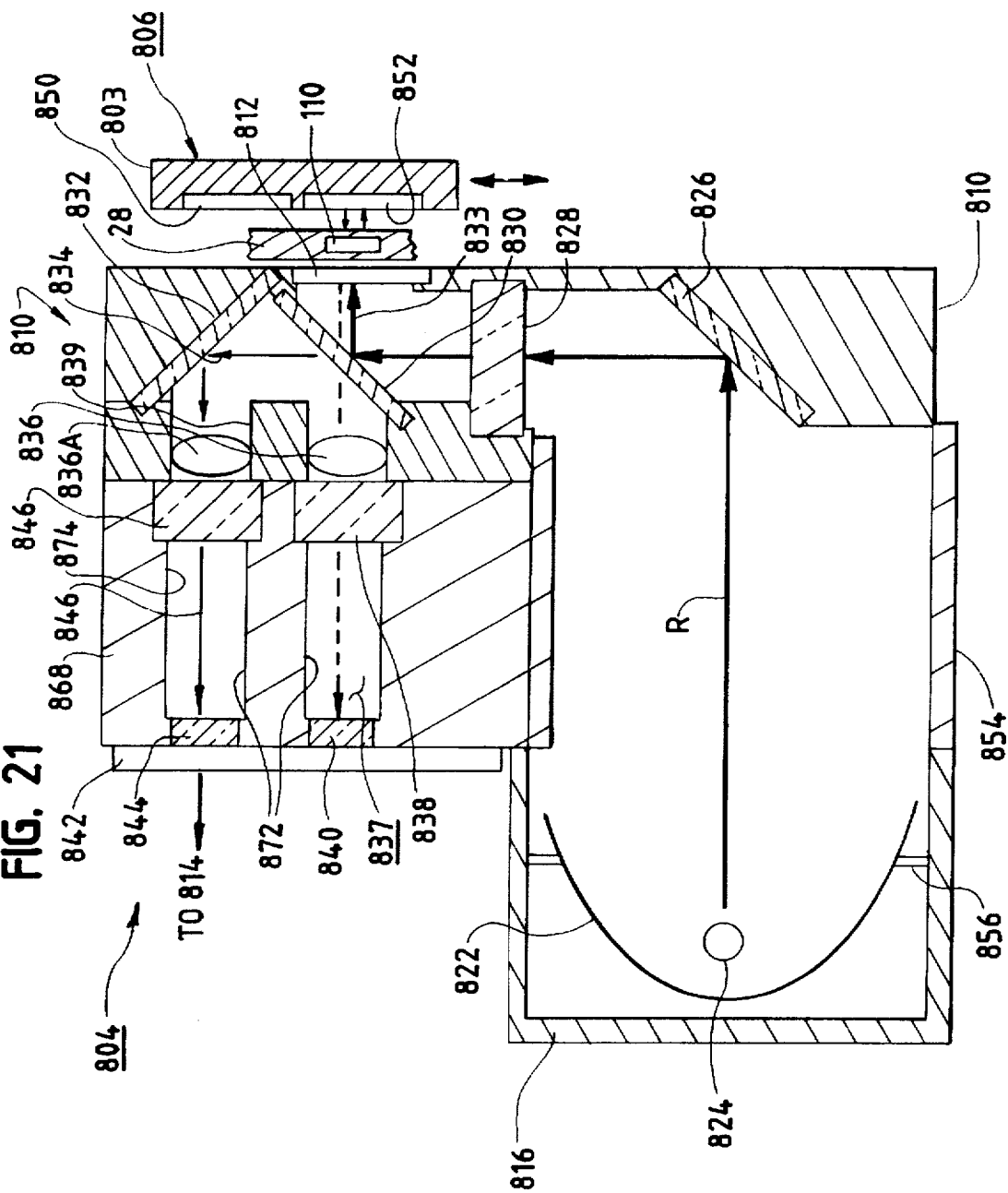
FIG. 21 is a sectional view of the fluorescence optical substation of FIG. 20.

Referring now to FIG. 21, the fluorescence optics substation 804 is shown in a sectional view perpendicular to the axis of the flash lamp 824 and the six photodiode detectors. The flash lamp cassette 816 houses the single elongate linear xenon lamp 824, which is mounted at the focus of an elongate cylindrical parabolic reflecting mirror 822. The flashlamp 824 has a high current capacity connection allowing field replacement of the lamp. This is unique for this lamp type due to the high pulse currents generated during the flash (over 350 amps).

The flash lamp radiation R is reflected off of a cold mirror 826 onto a 365 nM filter 828, which filters the radiation R to pass radiation at the excitation wavelength of the fluorophores. After passing through the filter 828, the radiation R reflects off a dichromatic beam splitter 830 along its optical path 833 and out of the apertures 812 and into the card wells 110. Any radiation passing through the wells 110 is reflected off the reflector 852 in the reflector assembly 806 and reflected back into the wells 110. The radiation excites the fluorophores in the well 110, causing the fluorophore to briefly to emit radiation. The emission radiation is shown as a dashed line in FIG. 21. The emission radiation passes through the dichromatic beam splitter 830, through a focusing lens 836 and band pass filter 838 onto a photodiode detector 840. There are six photodiode detectors in all for the six optical channels.

The use of a selective reflector 852 enhances the signal-to-noise ratio and minimizes optical cross-talk by doubling the optical path. Further, when the card 28 is positioned for reading by the fluorescence station by means of the optical interrupt, the wells in the card are oriented to minimize cross-talk and maximize the fluorescence signal. The card 28 material is preferrably opaque to minimize cross-talk, and white to maximize the fluorescence signal.

The dichromatic beam splitter 830 is highly reflective to radiation at the excitation wavelength of the fluorophores, reflecting approximately 95% of the radiation into the well 110. However, the dichromatic beam splitter 830 is highly transmissive to radiation at the emission wavelength of the fluorophores, passing most of the radiation from the fluorophore along the same optical path 833 onto the detectors 840.

Approximately 5% of the radiation from the lamp 824 that is not reflected off the dichromatic beam splitter 830 is transmitted along an optical path 834 to a mirror 832. The mirror 832 reflects the radiation through a focusing lens 836A and a band pass filter 846 to a reference photodiode detector 844. The reference detector 844 is used by the peak detector circuit 814 to compute the ratio of the signal detected by the detectors 840 divided by the signal detected by reference detector 844. The output of the lamp 824 may vary over time, however the ratio of the output of the channel 840 detector divided by the output of the reference detector 844 remains constant, i.e., independent of changes in lamp output over time.

In addition to compensating for changes in lamp intensity, the reference channel 844 can also be used to determine if the lamp 824 is providing sufficient light for proper operation of the fluorescence optical system. By monitoring the lamp output at the reference detector 844, the system can automatically determine when the lamp 824 needs to be changed.

Still referring to FIG. 21, the reflector assembly 806 also includes a solid reference 850 which emits radiation at the fluorophore emission wavelength when the reference 850 is moved into the optical path 833. Preferably, the solid reference 850 is a phosphorescent Europium source sandwiched between glass plates and having a 450 nM filter placed over the front surface of the glass.

The peak detector 814 inputs signals from the six photodiode detectors to a set of six fixed gain amplifiers that convert the current from the photodiode to a voltage signal. The lamp reference channel input signal is supplied to a detector and amplifier. The output of the detectors and fixed gain amplifiers are input into a set of variable gain amplifiers. Similarly, the output of the detector amplifier is input to a variable gain amplifier. The variable gain amplifiers supply an output signal to a set of electronic peak detectors.

The electronic peak detectors are all basically the same as the peak detector described in the standard textbooks, but modified slightly in that a transconductance amplifier is used as the first stage amplifier, instead of a standard operational amplifier. This allows the circuit to operate very fast with a minimum of signal distortion over several decades of voltage.

The output of the peak detectors is buffered by a buffer amplifier and supplied to a multichannel input Analog to Digital (A-D) converter. The output of the peak detector from the reference channel is similarly buffered and supplied to a reference input in the A-D converter. A data bus is provided which sends the output of the A-D converter to a microprocessor-based controller board (not shown) which conducts the processing of the signals from the six channels and the reference photodetector. In particular, the controller board takes the ratio of the output of the six channels divided by the output of the reference channel, to thereby compute a relative fluorescence number which is independent of the output of the lamp 824.

Once the card 28 is positioned in the fluorescence substation, the lamp 824 is flashed at a 25 Hz rate a number of times, such as ten times. After each flash, the A-D converter computes the ratio of each channel to the reference and the controller board reads the results. After 10 flashes, the results are signal processed for each channel. This process in conducted in parallel for each of the six channels.

The data bus also supplies control signals to the peak detectors and the variable gain amplifiers. In the calibration of the detectors, the controller board adjusts the variable gain amplifiers so as to provide a uniform amplitude across the six channels.

Transmittance Substation 802

Figure 22:
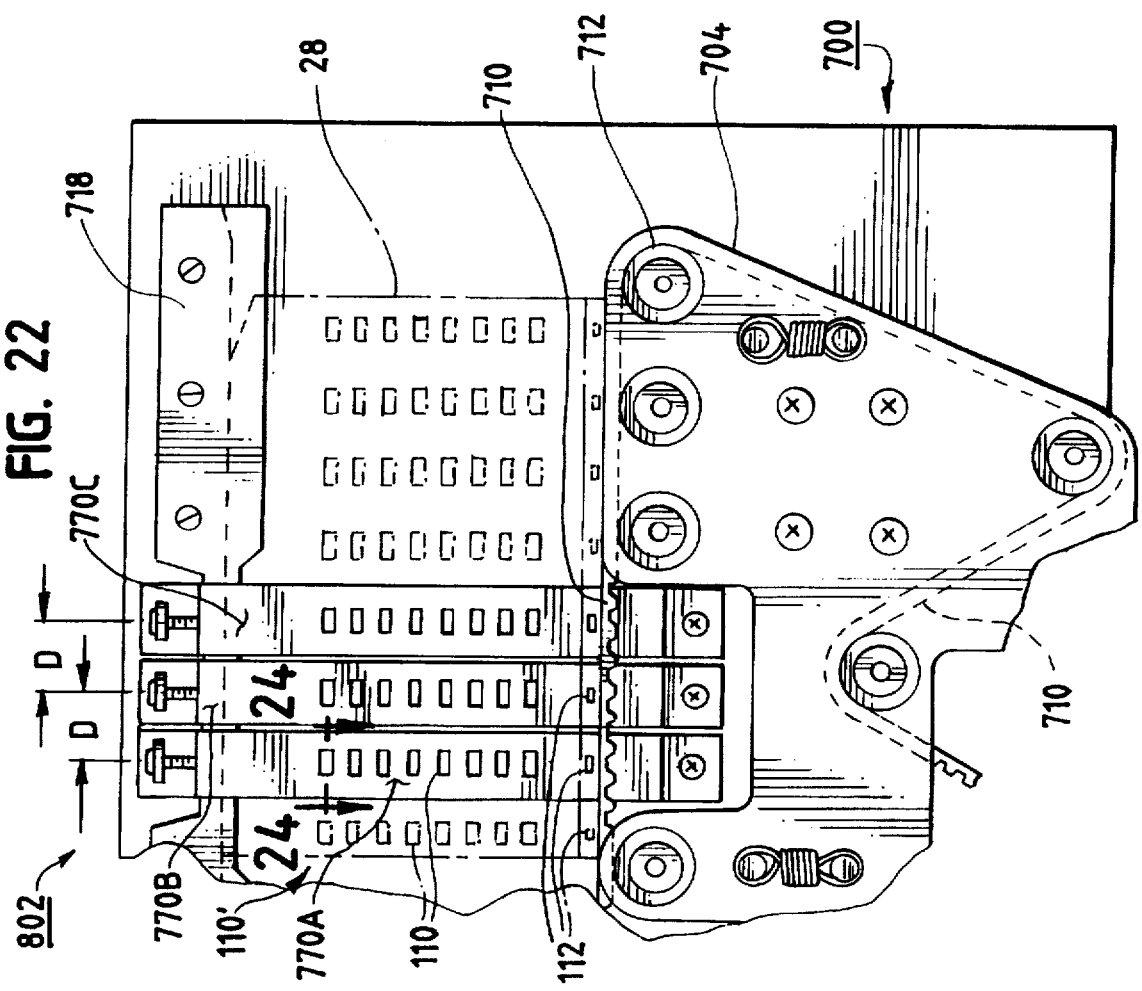
FIG. 22 is a detailed elevational view of the transmittance substation of FIG. 3.

Referring now to FIG. 22, a preferred transmittance substation 802 is shown in an elevational view. The substation 802 has up to three transmittance optical sources 770A, 770B and 770C, each of which comprise eight LED sources (one for each well in a column of wells) and an optical interrupt LED source. The optical sources 770A–C are separated from each other by a separation distance D equal to the separation distance between the columns of wells 110 in the card 28. Three sources 770A–C are provided so as to enable transmittance testing at three different sets of wavelengths. The source 770A is shown in perspective view in FIG. 23, and has eight LEDS 797 which are separated from each other by a distance L equal to the distance between adjacent wells 110 in the column direction of the card 28. The optical interrupt LED 789 shines light throughout the optical interrupt 112 along the base of the card 28. A set of three columns of transmittance detectors are placed behind the three sources 770A–C to collect radiation from the LEDs 797 and 789 and supply transmission data to the controller board in a well-known manner.

Referring now to FIG. 24, the transmittance source 770A and its associated detector 791 are shown in a sectional view, taken along the lines 24—24 in FIG. 22. The LED source 797 is mounted to a substrate 798 in a well known manner and transmits light through the aperture 793 to the sample well 110. The radiation falls on the photodiode detector 791, which is also mounted to a substrate 792 in a well known manner. The detector 791 is mounted in a housing 795 that extends vertically directly opposite the detector 770A. The construction of light source 770A and detector 795 is the same for the other two sources and detectors in the transmittance station 802.

To perform transmittance analysis of the entire well 110, the card 28 is moved rapidly in a series of small increments relative to the source 770A, for example in 10 or 14 positions, and multiple illuminations of the well 110 are taken at each position. A presently preferred transmittance illumination test is fourteen equidistant positions across the entire width of the well 110, and 10 illumination events at each of the fourteen positions. This test can be performed at up to three different transmittance wavelengths for every well, resulting in a large set of transmittance data.

Figure 23:
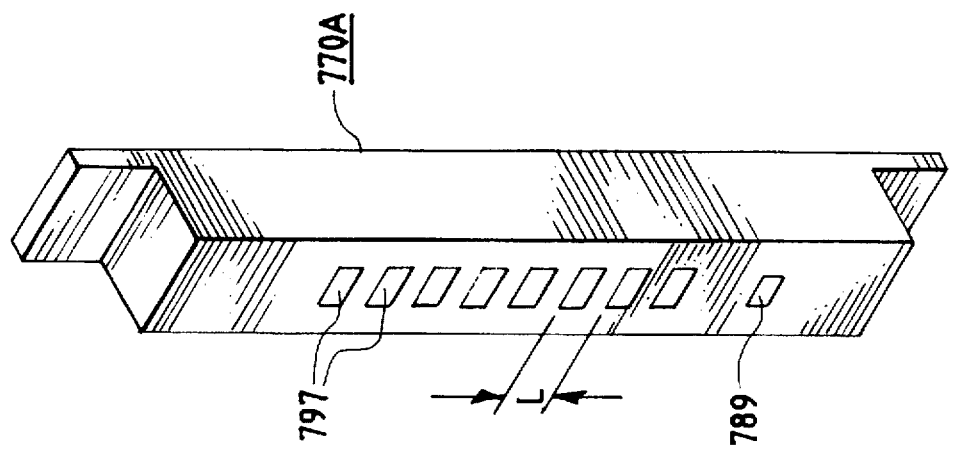
FIG. 23 is a perspective view of one of the LED transmittance sources of FIG. 22.

Referring to FIG. 23, as the card 28 is moved out of the carousel 604, the first column 110' in the card is moved to the source 770C having LEDs of a first wavelength, whereby the 14 movement steps and 10 illumination events per step are performed. The card 28 is then advanced such that column 110' is positioned opposite the source 770B having LEDs of a second wavelength. The source 770B illuminates the first column 110' while the source 770C illuminates the second column. The card 28 is then moved such that the column 110' is positioned opposite the source 770A having LEDs of a third wavelength, and now sources 770A–C all operate in concert to illuminate three columns of the wells simultaneously. The card 28 is advanced to the left such that all columns are subject to transmittance illumination at the three sets of wavelengths. A column of LEDS could contain up to eight different wavelengths in one column if desired. When the last column has been illuminated by source 770A, the card 28 is moved to the fluorescence substation 804 for fluorescence testing.

Of course, the operation of the transport system 700 and transmittance substation 802 could be controlled such that the card 28 is moved throughout the station 802 from left to right instead of right to left. Further, a lesser or even greater number of transmittance sources 770 could be used if desired.

Cassette Identification and Bar Code Reading Systems

A. Cassette Identification System

Referring to FIG. 26, in a preferred embodiment a stand-alone cassette identification station 80 is provided to facilitate the processing of the cards 28 by the machine 20. The station 80 consists of a computer terminal having a monitor 84 and attached keyboard 86 and bar code reader 88. A conventional host CPU and memory are contained in the station 80, which are not shown. The host CPU runs a menu-driven software program that prompts a technician to enter patient or sample information that is to be associated with each of the cards 28. The station 90 has a data port allowing it to communicate with the machine 20 or another computer.

The station 80 receives patient and sample data from the technician via a bar code scanner and/or keyboard 86, stores the information in its memory, and associates that information with the bar code 89 that is applied to the top of the test sample cards 28. The station 80 can have a bar code reader 88 that reads the bar codes 89 applied to the cards 28. After the cards have been read, the user is prompted to scan or enter the patient or other information that is associated with the cards 28. Bar code cards 83 may be provided with the most commonly entered data to minimize the typing in of information. After each card 28 has been read and the information associated with it loaded into the computer at the station 80, the technician loads the card 28 into a cassette 26.

The base portion of the station 80 below the screen 84 is given a molded contour so as to snugly receive the cassette 26 and position the cassette 26 as shown, such that the two touch buttons mounted on the rear of the cassette 26 are placed into touching contact with the touch button data writing terminals 82 for the station 80. After all the cards 28 have been loaded into the cassette, the information associated with all the cards is loaded onto the touch buttons via the terminals 82. The cassette 26 is now ready to be loaded into a boat 22 in the machine 20.

Referring to FIG. 27, the touch buttons are read at an information retrieval station in the machine comprising touch button reader terminals 85 attached to the side of the center mount 34. As the boat 22 is moved along the base pan 24, the touch buttons come into contact with the reader terminals 85. The data from the touch buttons is passed via leads 87 to a central processing unit for the machine 20, which associates the data with the optical data from the optics station 800.

B. Bar Code Reading Station

Referring to FIGS. 3 and 28, the machine 20 further includes a bar code reading station 90 to read the bar codes 89 applied to the cards 28. The bar codes are read by a bar code reader 90 mounted to a bar code reader support structure 92 affixed to the center mount 34. The bar codes are applied to the cards 28 in a location such that when the cards 28 are loaded in the cassette 26, the bar codes are along the "top" of the card 28, where they can be more easily read.

As the boat 22 and cassette 26 are advanced to the left along the front of the machine 22, they pass underneath a card separation device 94 consisting of wheel 94 mounted to a support piece 96. The support piece 96 is mounted via a pin 98 to a bulkhead attached to the center mount 34. The support piece 96 is allowed to pivot about the pin 98 as shown by the arrow in FIG. 28, permitting the wheel 94 to ride up and over the cards as the cards 28 pass underneath the wheel 94. In the process of riding up and over the cards 28, the wheel 94 rocks or pushes the cards into a slanted position as shown in FIG. 28, where they can be more easily read by a bar code reader 90. Referring to FIG. 28 in particular, as card 28C passes under the wheel 94, the wheel pushes the card 28C in its slot to the slanted orientation shown. The wheel 94 rides up and over the top of the card and performs the same operation on the next card 28D, pushing card 28D in to the position 28E shown in dashed lines. The wall 70 height and distance between adjacent walls 70 in the cassette 26 is chosen so as to permit enough rocking motion for the cards 28, but not so much so as to create too much play in the positioning of the cards 28 in the cassette 26.

The bar code reader 90 station is positioned along the front side of the machine between the loading station and the diluting station 200. In this position, the reading station is able to check the validity of the test prior to filling the card with the sample. This allows the test sample to be saved in the event of an operator or instrument error.

User Interface

While the foregoing discussion and illustrations for the machine 20 have described in detail of the construction and operation of the machine 20, it will be understood that the machine per se has a user friendly and attactive panel covering for aestetic and safety purposes. A user interface connected to the machine's host CPU is preferrably included on the front panel, and includes a LCD (liquid crystal display) screen and touch pad for presenting instrument status information to the operator. It is also used for things such as start tests, request information, and perform diagnostics.

A preferred test sample card 28 for the machine 20 is described in application Ser. No. 08/455,534, filed May 31, 1995, now U.S. Pat. No. 5,609,828, which is incorporated by reference herein.

A presently preferred embodiment of the invention has been described. Persons of skill in the art will appreciated the variations and modifications can be made to the particular details without departure from the true spirit and scope of the invention. This true spirit and scope of the invention is defined by the appended claims, to be interpreted in light of the foregoing.

We claim:

1. A machine for automatically testing a sample delivered to a reagent-filled test card, comprising:
    a loading station and a tray moveable within said machine for receiving at least one test sample and at least one test card, wherein at least one test sample is placed in fluid communication with at least one test card in said tray;
    a vacuum station having a vacuum chamber moveable relative to said tray between upper and lower positions, said chamber cooperating with said tray to make a sealing engagement with said tray in said lower position, said vacuum station having means for supplying a vacuum to said chamber and releasing said vacuum to atmosphere, thereby loading said sample into said test card;
    a sealing station for sealing said test card after loading of said test card;
    an incubation station for incubating said test card;
    an optical reading station for reading said test card;
    a test sample positioning system for moving said test card from said loading station to said vacuum station, from said vacuum station to said incubation station, and for moving said test card from said tray into said incubation station; and
    a test card transport station for transporting said test card from said incubation station to said optical reading station, said optical reading station conducting optical analysis of said sample loaded into said test card.

2. The machine of claim 1, wherein said sample is carried by an open receptacle in said tray, and wherein said machine further comprises a fluid addition station supplying a predetermined volume of fluid to said receptacle.

3. The machine of claim 2, wherein said fluid addition station adds a diluent to said receptacle.

4. The machine of claim 2, wherein said fluid addition station adds a reagent to said receptacle.

5. The machine of claim 1, wherein said tray carries a plurality of samples supplied in a plurality of open receptacles, and wherein said machine further comprises a pipetting station for automatically transferring fluid from one receptacle to another receptacle in said tray.

6. The machine of claim 5, wherein said pipetting station transfers said fluid with a disposable straw, and wherein said pipetting station has a hopper for storing said straws and means for automatically removing said straws one at a time from said hopper.

7. The machine of claim 5, wherein said machine further comprises a diluting station adding a predetermined quantity of diluent to at least one of said receptacles containing said samples.

8. An automated microbiological testing system for testing test sample fluids containing microbiological samples, said test sample fluids contained in open receptacles, said system for use in conjunction with test sample cards having a plurality of sample wells, said test sample cards comprising susceptibility cards and identification cards, the system comprising:
    a base pan;
    a tray for carrying said receptacles and said test sample cards across said base pan;
    a diluting station for adding a predetermined volume of a fluid to at least one of said receptacles;
    a pipetting station for transferring test sample fluid from one of said receptacles in said tray to another of said receptacles in said tray;
    a vacuum station moveable with respect to said tray and cooperating with said tray to form a vacuum enclosure around said receptacles and said test sample cards, said vacuum station filter comprising a vacuum source for loading said test sample fluids into said wells of said test sample cards;
    a sealing station for sealing said test sample cards after loading of said test sample cards;
    an incubation station for incubating said test sample cards;
    a reading system for conducting optical analysis of said wells in said test sample cards;
    a positioning system for moving said tray over said base pan from said vacuum station to said incubation station and for loading said test sample cards from said tray into said incubation station; and
    means for moving said cards from said incubation station to said reading station.

9. The system of claim 8, wherein said diluting station adds a diluent to a first receptacle in fluid communication with a susceptibility card in said tray;
    said pipetting station withdraws a fluid containing a microbiological sample from a second receptacle in said tray, said second receptacle in fluid communication with an identification card, and
    said pipetting station transfers said fluid containing said microbiological sample to said first receptacle;
    said vacuum station operative to load said identification card and said susceptibility card with said fluids in said first and second receptacles and said reading system operative to read said susceptibility and identification cards whereby identification and susceptibility analysis may be obtained of said microbiological sample automatically.

10. The system of claim 8, further comprising a stacking disposal station having a tray removable from said machine receiving said cards after reading of said cards by said optical system and means for maintaining said cards in a stacked condition in said magazine.

* * * * *